United States Patent
Lee et al.

(10) Patent No.: US 10,351,839 B2
(45) Date of Patent: Jul. 16, 2019

(54) LYSINE DECARBOXYLASE HAVING IMPROVED STABILITY WITH A PH CHANGE, MICROORGANISM COMPRISING A POLYNUCLEOTIDE ENCODING THE SAME, AND METHOD FOR PRODUCING CADAVERINE USING THE SAME

(71) Applicant: CJ CHEILJEDANG CORP., Seoul (KR)

(72) Inventors: Jae Hun Lee, Seoul (KR); Young Lyeol Yang, Seoul (KR); Bo Seong Park, Gimpo-si (KR); Yean Hee Park, Seoul (KR); Jin Seung Park, Seoul (KR); Byeo Ri An, Seoul (KR); In Seok Oh, Seoul (KR); Na Hum Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/549,792

(22) PCT Filed: Jan. 14, 2016

(86) PCT No.: PCT/KR2016/000389
§ 371 (c)(1),
(2) Date: Aug. 9, 2017

(87) PCT Pub. No.: WO2016/129812
PCT Pub. Date: Aug. 18, 2016

(65) Prior Publication Data
US 2018/0030430 A1 Feb. 1, 2018

(30) Foreign Application Priority Data
Feb. 9, 2015 (KR) .................. 10-2015-0019732

(51) Int. Cl.
*C12N 9/88* (2006.01)
*C12P 13/00* (2006.01)
*C12N 15/70* (2006.01)

(52) U.S. Cl.
CPC ............... *C12N 9/88* (2013.01); *C12N 15/70* (2013.01); *C12P 13/00* (2013.01); *C12P 13/001* (2013.01); *C12Y 401/01018* (2013.01)

(58) Field of Classification Search
None
See application file for complete search history.

(56) References Cited

U.S. PATENT DOCUMENTS

| 7,794,726 B2 | 9/2010 | Levine |
| 2011/0039313 A1 | 2/2011 | Verseck et al. |
| 2011/0177551 A1 | 7/2011 | Mimitsuka et al. |
| 2011/0250637 A1 | 10/2011 | Kurihara et al. |
| 2014/0004576 A1 | 1/2014 | Sasaki et al. |

FOREIGN PATENT DOCUMENTS

| EP | 1482055 A1 | 12/2004 |
| JP | 2004000114 A | 1/2004 |
| JP | 2008193898 A | 8/2008 |
| JP | 2010098998 A | 5/2010 |
| JP | 2013146269 A | 8/2013 |
| JP | 2015216894 A | 12/2015 |
| KR | 1020120021491 A | 3/2012 |
| RU | 2513694 C2 | 11/2012 |
| RU | 2516792 C2 | 1/2013 |
| WO | 2008142034 A2 | 11/2008 |
| WO | 2014113999 A1 | 7/2014 |
| WO | 2015196430 A1 | 12/2015 |

OTHER PUBLICATIONS

GenBank Accession No. WP_017938426. Jun. 28, 2013.*
Xu et al. Amino Acids. Sep. 2014;46(9):2165-75.*
Ma et al. Biotechnol Lett. Apr. 2015;37(4):799-806. Epub Dec. 17, 2014.*
Li et al. J Ind Microbiol Biotechnol. Apr. 2014;41(4):701-9.*
Accession U3B3K0. Nov. 13, 2013.*
Chica et al. Curr Opin Biotechnol. Aug. 2005;16(4):378-84.*
Singh et al. Curr Protein Pept Sci. 2017, 18, 1-11.*
Accession U3H3I6—Alignment to Seq ID No. 3. Nov. 13, 2013 (Year: 2013).*
Accession S6AXK8. Oct. 16, 2013. (Year: 2013).*
Accession I4L6N3. Sep. 5, 2012. (Year: 2012).*
Gale E.F., et al., "Studies on Bacterial Amino-acid Decarboxylases", Apr. 10, 1944, Biochemical J. 38, pp. 232-242.
International Search Report with English Translation for International Application No. PCT/KR2016/000389 dated Apr. 20, 2016.
lysine decarboxylase [Pseudomonas alcaligenes]. NCBI GenBank Accession Reference Sequence No. WP_021221793.1 [retrieved on Mar. 29, 2016] pp. 1-2. Retrieved from the Internet: <URL: https://www.ncbi.nlm.nih.gov/protein/544804658?report=genbank&log$=protalign&b.
lysine decarboxylase [Pseudomonas thermotolerans]. NCBI GenBank Accession Reference Sequence No. WP_017938426.1 [retrieved on Mar. 29, 2016] pp. 1-2. Retrieved from the Internet: <URL: http://www.ncbi.nlm.nih.gov/protein/516562995?report=genbank&log$=protalign&b.
Manuel, et al., "Cadaverine Suppresses Persistence to Carboxypenicillins in Pseudomonas aeruginosa PAO1", Antimicrobial Agents and Chemotherapy, vol. 54, No. 12, pp. 5173-5179 (Dec. 2010).
NCBI GenBank Accession Reference Sequence No. WP_005788744.1: lysine decarboxylase [Pseudomonas synxantha] pp. 1-3 (May 28, 2013).

(Continued)

*Primary Examiner* — Christian L Fronda

(74) *Attorney, Agent, or Firm* — Cantor Colburn LLP

(57) ABSTRACT

The present invention relates to: a novel lysine decarboxylase; a microorganism transformed with a gene coding for the activity concerned; and a method for producing cadaverine by using the same.

8 Claims, 12 Drawing Sheets
Specification includes a Sequence Listing.

(56) References Cited

OTHER PUBLICATIONS

NCBI GenBank Accession Reference Sequence No. WP_016493540.1: putative Orn/Arg/Lys decarboxylase [Pseudomonas resinovorans] pp. 1-3 (Jun. 17, 2013).
NCBI GenBank Accession Reference Sequence No. WP_023047507.1: lysine decarboxylase [Pseudomonas putida] pp. 1-2 (Oct. 24, 2011).
Written Opinion for International Application No. PCT/KR2016/000389 dated Apr. 20, 2016.
Joseph Sambrook et al., Molecular Cloning A Laboratory Manual, 1989, 21 pages, vol. 1, Cold Spring Harbor Laboratory Press.
Korean Office Action for Application No. 10-2015-0019732 dated Aug. 28, 2017.
Enzyme Handbook, Asakura Shoten, Inc. 1982, pp. 636-637.
Zhi-Gang Qian et al., Metabolic Engineering of *Escherichia coli* for the Production of Cadaverine: A Five Carbon Diamine 2011, pp. 93-103, vol. 108, No. 1, Wiley Periodicals, Inc.
Takashi Mimitsuka et al., Metabolic Engineering of Corynebacterium glutamicum for Cadaverine Fermentation, 2007, pp. 2130-2135, vol. 71, No. 9, Biotechnol. Biochem.
Japanese Office Action for Application No. 2017-541814, dated Jul. 3, 2018.
Database Genbank WP 027896066.1, Sep. 21, 2013.
Office Action and Search Report dated May 24, 2018 of the Russian Patent Application No. 2017128752.
Partial European Search Report dated Jun. 8, 2018 of the European Patent Application No. 16749352.7.
Stefanie Kind, et al., "From zero to hero—Production of bio-based nylon from renewable resources using engineered Corynebacterium glutamicum", Metabolic Engineering 25 (2014) 113-123.
UniProtKB—U3H3I6 (U3H3I6_PSEAC), Nov. 13, 2013, found at www.uniprot.org/uniprot/U3H3I6.

* cited by examiner

Lysine
(2,6-diaminohexanoic acid)

Cadaverine
(1,5-pentanediamine
or pentamethylenediamine)

FIG. 2

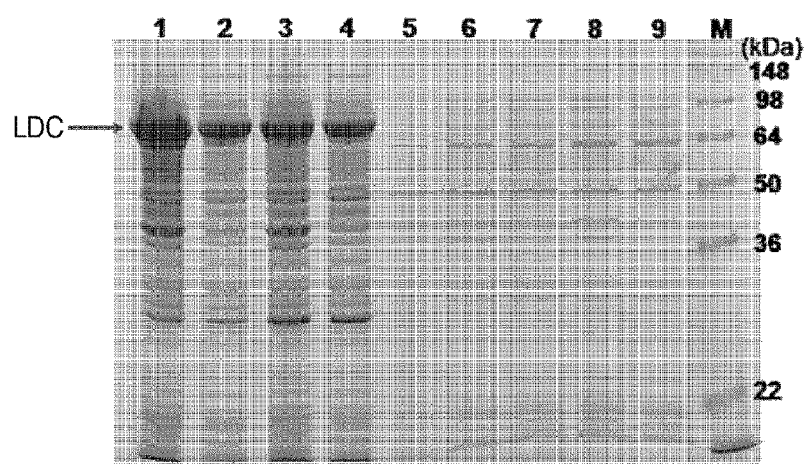

1: His-PtLDC expression at 18°C (cell lysate)
2: His-PtLDC expression at 18°C (soluble protein)
3: PtLDC expression at 18C° (cell lysate)
4: PtLDC expression at 18C° (soluble protein)
5: His-PtLDC expression with chaperones at 37C° (cell lysate)
6: His-PtLDC expression with chaperones at 37C° (cell lysate)
7: His-PtLDC expression with chaperones at 37C° (soluble protein)
8: PtLDC expression with chaperones at 37C° (cell lysate)
9: PtLDC expression with chaperones at 37C° (soluble protein)
M: marker M: marker
1: PaLDC expression (cell lysate)
2: PaLDC expression (soluble protein)
3: PrLDC expression (cell lysate)
4: PrLDC expression (soluble protein)

TEMPERATURE (°C)

pH

M: marker
1: EcLDC expression (cell lysate)
2: EcLDC expression (soluble protein)
3: PpLDC expression (cell lysate)
4: PpLDC expression (soluble protein)
5: PtLDC expression (cell lysate)
6: PtLDC expression (soluble protein)
7: PxLDC expression (cell lysate)
8: PxLDC expression (soluble protein)

SEQUENCE LISTING

<160> NUMBER OF SEQ ID NOS: 24

<210> SEQ ID NO 1
<211> LENGTH: 751
<212> TYPE: PRT
<213> ORGANISM: Pseudomonas thermotolerans
<220> FEATURE:
<221> NAME/KEY: PEPTIDE
<222> LOCATION: (1)..(751)
<223> OTHER INFORMATION: Lysine decarboxylase from Pseudomonas
      thermotolerans (PtLDC)

<400> SEQUENCE: 1

Met Tyr Lys Asp Leu Gln Phe Pro Ile Leu Ile Val His Arg Asp Ile
 1               5                  10                  15

Lys Ala Asp Thr Val Ala Gly Asn Arg Val Arg Glu Ile Ala Arg Glu
                20                  25                  30

Leu Glu Gln Asp Gly Phe Ala Ile Leu Ser Thr Ala Ser Ala Ser Glu
            35                  40                  45

Gly Arg Ile Val Ala Ser Thr His His Gly Leu Ala Cys Ile Leu Val
        50                  55                  60

```
Ala Ala Glu Gly Ala Gly Glu Asn Arg Ser Leu Leu Gln Asp Val Val
 65              70                  75                  80

Glu Leu Ile Arg Val Ala Arg Val Arg Ala Pro Gln Leu Pro Ile Phe
             85                  90                  95

Ala Leu Gly Glu Gln Val Thr Ile Glu Asn Ala Pro Ala Glu Ala Met
            100                 105                 110

Ala Asp Leu Asn Gln Leu Arg Gly Leu Leu Tyr Leu Phe Glu Asp Thr
            115                 120                 125

Val Pro Phe Leu Ala Arg Gln Val Ala Arg Ala Arg Gly Tyr Leu
130                 135                 140

Glu Gly Leu Leu Pro Pro Phe Arg Ala Leu Val Glu His Thr Ala
145                 150                 155                 160

Gln Ser Asn Tyr Ser Trp His Thr Pro Gly His Gly Gly Val Ala
                165                 170                 175

Tyr Arg Lys Ser Pro Val Gly Gln Ala Phe His Gln Phe Gly Glu
                180                 185                 190

Asn Thr Leu Arg Ser Asp Leu Ser Val Ser Val Pro Glu Leu Gly Ser
            195                 200                 205

Leu Leu Asp His Thr Gly Pro Leu Ala Glu Ala Glu Thr Arg Ala Ala
210                 215                 220

Arg Asn Phe Gly Ala Asp His Thr Tyr Phe Val Ile Asn Gly Thr Ser
225                 230                 235                 240

Thr Ala Asn Lys Ile Val Trp His Ser Met Val Gly Arg Asp Asp Leu
                245                 250                 255

Val Leu Val Asp Arg Asn Cys His Lys Ser Ile Leu His Ala Ile Ile
            260                 265                 270

Met Thr Gly Ala Ile Pro Leu Tyr Leu Cys Pro Glu Arg Asn Glu Leu
            275                 280                 285

Gly Ile Ile Gly Pro Ile Pro Leu Ser Glu Phe Ser Lys Glu Ala Ile
            290                 295                 300

Gln Ala Lys Ile Ala Ala Ser Pro Leu Ala Arg Gly Arg Glu Pro Arg
305                 310                 315                 320

Val Lys Leu Ala Val Val Thr Asn Ser Thr Tyr Asp Gly Leu Cys Tyr
                325                 330                 335

Asn Ala Glu Met Val Lys Gln Ala Leu Gly Asp Ser Val Glu Val Leu
            340                 345                 350

His Phe Asp Glu Ala Trp Tyr Ala Tyr Ala Ala Phe His Glu Phe Tyr
            355                 360                 365

Ala Gly Arg Tyr Gly Met Gly Thr Arg Leu Glu Ala Asp Ser Pro Leu
            370                 375                 380

Val Phe Ala Thr His Ser Thr His Lys Leu Leu Ala Ala Phe Ser Gln
385                 390                 395                 400

Ala Ser Met Ile His Val Arg Asp Gly Gly Ser Arg Lys Leu Asp Arg
                405                 410                 415

Tyr Arg Phe Asn Glu Ala Phe Met Met His Ile Ser Thr Ser Pro Gln
            420                 425                 430

Tyr Ser Ile Leu Ala Ser Leu Asp Val Ala Ser Ala Met Met Glu Gly
            435                 440                 445

Pro Ala Gly Arg Ser Leu Ile Gln Glu Thr Phe Asp Glu Ala Leu Ser
    450                 455                 460

Phe Arg Arg Ala Leu Ala Asn Leu Arg Gln Asn Leu Pro Ala Asp Asp
465                 470                 475                 480
```

```
Trp Trp Phe Asp Ile Trp Gln Pro Pro Arg Ala Ala Gly Val Glu Glu
                485                 490                 495

Val Ala Thr Arg Asp Trp Leu Leu Glu Pro Asn Ala Glu Trp His Gly
            500                 505                 510

Phe Gly Glu Val Asn Asp Asp Tyr Val Leu Leu Asp Pro Val Lys Val
        515                 520                 525

Thr Leu Val Thr Pro Gly Leu Ser Ala Gly Gly Arg Leu Asp Glu His
    530                 535                 540

Gly Ile Pro Ala Ala Val Val Ser Lys Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Leu Thr Glu Leu Leu Glu
            580                 585                 590

Phe Lys Arg Leu Tyr Asp Ala Asn Val Ala Leu Ala Glu Ala Leu Pro
        595                 600                 605

Ser Ile Ala Arg Ala Gly Gly Thr Arg Tyr Ala Gly Met Gly Leu Arg
    610                 615                 620

Asp Leu Cys Asp Glu Leu His Ala Cys Tyr Arg Glu Asn Ala Thr Ala
625                 630                 635                 640

Lys Ala Leu Lys Arg Met Tyr Thr Thr Leu Pro Glu Val Val Met Lys
                645                 650                 655

Pro Ala Asp Ala Tyr Asp Arg Leu Val Arg Gly Val Glu Ala Val
            660                 665                 670

Pro Ile Asp Arg Leu Glu Gly Arg Ile Ala Ala Val Met Leu Val Pro
        675                 680                 685

Tyr Pro Pro Gly Ile Pro Leu Ile Met Pro Gly Glu Arg Phe Thr Gln
    690                 695                 700

Ala Thr Arg Ser Ile Ile Asp Tyr Leu Gly Phe Ala Arg Asp Phe Asp
705                 710                 715                 720

Arg Arg Phe Pro Gly Phe Asp Ala Asp Val His Gly Leu Gln Ser Glu
                725                 730                 735

Glu Arg Gly Gly Glu Arg Cys Tyr Thr Val Asp Cys Ile Lys Ile
            740                 745                 750

<210> SEQ ID NO 2
<211> LENGTH: 2256
<212> TYPE: DNA
<213> ORGANISM: Pseudomonas thermotolerans
<220> FEATURE:
<221> NAME/KEY: gene
<222> LOCATION: (1)..(2256)
<223> OTHER INFORMATION: Lysine decarboxylase gene from Pseudomonas
      thermotolerans (ptldc)

<400> SEQUENCE: 2
atgtacaaag acctccaatt ccccattctc atcgtccatc gcgacatcaa ggccgatacc     60
gtggccggca accgcgtccg tgagatcgcc cgcgaactgg aacaggacgg cttcgccatc    120
ctctccacgg caagtgccag cgaagggcgc atcgtcgctt ccacccacca tggtctggcc    180
tgcatcctgg tcgccgccga gggagcggga gagaatcgaa gctgctgca ggacgtggtg    240 gagctgatcc gcgtggccag ggtccgtgcg ccgcagctgc cgatcttcgc tctcggcgag    300
caggtgacca tcgagaacgc tccggccgag gccatggccg acctcaacca actgcgcggg    360
ctgctctacc tgttcgagga caccgtgccc ttcctcgccc gtcaggtggc gcgggccgcg    420
cgtggctacc tggagggggct gctgccgccg ttcttccgcg ccctggtgga gcacaccgcg    480
```

-continued

```
cagtccaact attcctggca cacccegggg cacggcggcg gtgtggctta ccgcaagagc    540
ccggtggggc aggcctttca ccagttcttc ggcgagaaca ccctgcgctc cgacttgtcg    600
gtttccgtac cggagctggg ttcgctgctg atcacaccg ggccgctggc cgaggcggaa     660
acccgcgcgg cgcgcaactt cggcgccgac catacctatt tcgtgatcaa cggcacctcg    720
acggccaaca agatcgtctg gcactccatg gtcggccgcg acgatctggt gttggtggac    780
cgcaactgcc acaagtcgat cctccacgcc atcatcatga ccggtgccat ccccctgtac    840
ctgtgcccgg agcgcaacga gctgggcatc atcgggccga ttccgctctc gagttcagc    900
aaggaggcga tccaggcgaa gatcgccgcc agcccgctgg ccagagggcg cgagccgcgg    960
gtcaagctgg cggtggtgac caattccacc tacgacggcc tctgttacaa cgccgagatg   1020
gtcaagcagg ccctcggcga cagcgtcgag gtgctgcact cgacgaggc ctggtacgcc    1080
tacgcggcct ccacgagtt ctacgcgggg cgttacggca tgggcactcg cctggaggcg    1140
gactcgcctc tggtctttgc cacccattcc acccacaagc tgctggctgc cttcagccag   1200
gcctcgatga ttcacgtgcg cgacggcggt agccgcaagc tggaccggta ccgcttcaac   1260
gaggccttca tgatgcacat ctccacctcg ccgcagtaca gcatcctcgc ctcgctggac   1320
gtggcctcgg cgatgatgga gggaccggcc gggcgctcgc tgatccagga aaccttcgat   1380
gaagcgctga gcttccgccg tgctctggcc aacctgcgcc agaacctgcc ggcggacgac   1440
tggtggttcg acatctggca gccgccgcgc gctgctggtg tcgaggaggt ggcgacccgc   1500
gactggctgc tggagccgaa tgccgagtgg cacggcttcg gcgaggtgaa cgacgactac   1560
gtgctgctcg atccggtcaa ggtcaccctg gtcaccccgg ggctgagcgc cggcgggcgc   1620
ctggacgagc acggcattcc cgccgcggtg gtcagcaagt tcctctggga acgcggcctg   1680
gtggtggaga agaccggcct gtactccttc ctggtgttgt tctccatggg gatcaccaag   1740
ggcaagtgga gcaccctgct caccgagctg ctggagttca gcgcctcta cgacgccaac   1800
gtggcgcttg ccgaggcgtt gccgagcatc gcccgcgccg gtggcacccg ctatgccggc   1860
atgggcctgc gcgacctgtg cgacgagctg cacgcctgct accggagaa cgccaccgcc   1920
aaggccctca agcgcatgta caccacgctc cccgaggtgg tgatgaagcc tgccgatgcc   1980
tacgaccggc tggtccgcgg agaggtggag gcggtgccca tcgaccgtct ggaaggacga   2040
atcgccgcg tgatgctggt gccctatccg ccgggcattc cgctgatcat gccgggcgag   2100
cgcttcaccc aggcgacccg ttcgatcatc gactacctgg gtttcgcccg cgatttcgat   2160
cgccgcttcc ccggcttcga cgcggacgtg cacgcctgc agagcgagga gcgcggcggc   2220
gagcgatgct acacggtgga ctgcatcaag atctga                             2256
```

<210> SEQ ID NO 3
<211> LENGTH: 751
<212> TYPE: PRT
<213> ORGANISM: Pseudomonas alcaligenes
<220> FEATURE:
<221> NAME/KEY: PEPTIDE
<222> LOCATION: (1)..(751)
<223> OTHER INFORMATION: Lysine decarboxylase from Pseudomonas
      alcaligenes (PaLDC)

<400> SEQUENCE: 3

Met Tyr Lys Asp Leu Lys Phe Pro Ile Leu Ile Val His Arg Asp Ile
1               5                   10                  15

Lys Ala Asp Thr Val Ala Gly Asp Arg Val Arg Gly Ile Ala Arg Glu
            20                  25                  30

```
Leu Glu Gln Asp Gly Phe Val Ile Leu Ser Thr Ala Ser Ser Ala Glu
         35                  40                  45

Gly Arg Ile Val Ala Ser Thr His His Gly Leu Ala Cys Ile Leu Val
         50                  55                  60

Ala Ala Glu Gly Ala Gly Glu Asn Gln Arg Leu Leu Gln Asp Val Val
 65                  70                  75                  80

Glu Leu Ile Arg Val Ala Arg Val Arg Ala Pro Gln Leu Pro Ile Phe
                 85                  90                  95

Ala Leu Gly Glu Gln Val Thr Ile Glu Asn Ala Pro Ala Glu Ala Met
                100                 105                 110

Ala Asp Leu Asn Gln Leu Arg Gly Leu Leu Tyr Leu Phe Glu Asp Thr
            115                 120                 125

Val Pro Phe Leu Ala Arg Gln Val Ala Arg Ala Arg Asn Tyr Leu
            130                 135                 140

Glu Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Val Ala
                165                 170                 175

Tyr Arg Lys Ser Pro Val Gly Gln Ala Phe His Gln Phe Gly Glu
            180                 185                 190

Asn Thr Leu Arg Ser Asp Leu Ser Val Ser Val Pro Glu Leu Gly Ser
            195                 200                 205

Leu Leu Asp His Thr Gly Pro Leu Ala Glu Ala Glu Ala Arg Ala Ala
            210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Ala Arg Asp Asp Leu
                245                 250                 255

Val Leu Val Asp Arg Asn Cys His Lys Ser Ile Leu His Ser Ile Ile
            260                 265                 270

Met Thr Gly Ala Ile Pro Leu Tyr Leu Ser Pro Glu Arg Asn Glu Leu
        275                 280                 285

Gly Ile Ile Gly Pro Ile Pro Leu Ser Glu Phe Ser Arg Glu Ser Ile
        290                 295                 300

Gln Ala Lys Ile Asp Ala Ser Pro Leu Ala Arg Gly Arg Ala Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Ala Leu Gly Asp Thr Val Glu Val Leu
            340                 345                 350

His Phe Asp Glu Ala Trp Tyr Ala Tyr Ala Ala Phe His Glu Phe Tyr
            355                 360                 365

Asp Gly Arg Tyr Gly Met Gly Thr Ala Arg Ser Glu Glu Gly Pro Leu
        370                 375                 380

Val Phe Thr Thr His Ser Thr His Lys Leu Leu Ala Ala Phe Ser Gln
385                 390                 395                 400

Ala Ser Met Ile His Val Gln Asp Gly Gly Ala Arg Gln Leu Asp Arg
                405                 410                 415

Asp Arg Phe Asn Glu Ala Phe Met Met His Ile Ser Thr Ser Pro Gln
            420                 425                 430

Tyr Gly Ile Ile Ala Ser Leu Asp Val Ala Ser Ala Met Met Glu Gly
        435                 440                 445
```

Pro Ala Gly Arg Ser Leu Ile Gln Glu Thr Phe Asp Glu Ala Leu Ser
    450                 455                 460

Phe Arg Arg Ala Leu Ala Asn Val Trp Gln Thr Leu Asp Ala Lys Asp
465                 470                 475                 480

Trp Trp Phe Asp Ile Trp Glu Pro Pro Gln Val Glu Gly Ala Glu Ala
                485                 490                 495

Val Ala Thr Gly Asp Trp Val Leu Glu Pro Gly Ala Asp Trp His Gly
            500                 505                 510

Phe Gly Glu Val Ala Asp Asp Tyr Val Leu Leu Asp Pro Ile Lys Val
        515                 520                 525

Thr Leu Val Thr Pro Gly Leu Ser Ala Asp Gly Lys Leu Gly Glu Gln
530                 535                 540

Gly Ile Pro Ala Ala Val Val Gly Lys Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Leu Thr Glu Leu Leu Glu
            580                 585                 590

Phe Lys Arg Ser Tyr Asp Ala Asn Ala Pro Leu Thr Ser Ala Leu Pro
        595                 600                 605

Ser Val Ala Arg Ala Asp Ala Ala Arg Tyr Gln Gly Leu Gly Leu Arg
610                 615                 620

Asp Leu Cys Asp Gln Leu His Ala Cys Tyr Arg Asp Asn Ala Thr Ala
625                 630                 635                 640

Lys Ala Met Arg Arg Met Tyr Thr Ala Leu Pro Glu Leu Ala Ile Lys
                645                 650                 655

Pro Ser Glu Ala Tyr Asp Lys Leu Val Arg Gly Glu Val Glu Ala Val
            660                 665                 670

Pro Ile Glu Gln Leu Gln Gly Arg Ile Ala Ala Val Met Leu Val Pro
        675                 680                 685

Tyr Pro Pro Gly Ile Pro Leu Ile Met Pro Gly Glu Arg Phe Thr Ala
690                 695                 700

Gln Thr Arg Ser Ile Ile Asp Tyr Leu Ala Phe Ala Arg Thr Phe Asp
705                 710                 715                 720

Ser Ala Phe Pro Gly Phe Asp Ser Asp Val His Gly Leu Gln His Asp
                725                 730                 735

Asp Ser Pro Met Gly Arg Cys Tyr Thr Val Asp Cys Ile Arg Glu
            740                 745                 750

<210> SEQ ID NO 4
<211> LENGTH: 2256
<212> TYPE: DNA
<213> ORGANISM: Pseudomonas alcaligenes
<220> FEATURE:
<221> NAME/KEY: gene
<222> LOCATION: (1)..(2256)
<223> OTHER INFORMATION: Lysine decarboxylase gene from Pseudomonas
      alcaligenes (paldc)

<400> SEQUENCE: 4
atgtacaaag acctgaagtt ccccatcctc atcgtccacc gcgacatcaa ggccgatacg      60
gtcgccggtg atcgcgtgcg cggcatcgcc cgcgaactgg agcaggacgg tttcgtcatc     120
ctctccaccg ccagttccgc cgaagggcgc atcgtcgcct ccacccacca cggcttggcc     180
tgcatcctcg tcgccgccga aggggcgggc gagaaccagc gcctgctgca ggacgtggtc     240
gagctgatcc gcgtggcccg ggtgcgtgcg ccgcaactgc cgatcttcgc cctgggcgaa     300

```
caggtgacca tcgagaacgc cccggccgaa gccatggccg acctcaacca gctgcgcggc      360
ctgctctacc tcttcgaaga caccgtgccc ttcctcgccc gccaggtcgc ccgcgccgcg      420
cgcaactacc tcgaaggcct gctgccgccg ttcttccgtg ccctggtgga gcacaccgcg      480
caatccaact actcctggca cacgcccggt cacggcggtg cgtcgcctca ccgcaagagc      540
ccggtggggc aggccttcca ccagttcttc ggcgaaaaca ccctgcgctc ggacctctcc      600
gtctcggtgc ccgagctggg ctcgctgctg atcacaccg gccccctggc cgaagccgag       660
gccccgcgccg cgcgcaactt cggtgctgac cacaccttct tcgtgatcaa cggcacctcc     720
accgcgaaca gatcgtctg gcactccatg gtcgcccgcg acgacctggt gctggtggac       780
cgcaactgcc acaagtcgat cctccactcg atcatcatga ccggcgccat cccgctctac     840
ctgagccccg agcgcaacga actgggcatc atcgggccca tcccctgag cgagttcagt      900
cgcgaatcga tccaggccaa gatcgacgcc agcccactgg cccggggccg cgcgcccaag     960
gtcaagctgg cggtggtgac caactccacc tacgacggcc tctgctacaa cgccgagctg    1020
atcaagcagg cgctgggcga caccgttgag gtgctgcact cgacgaagc ctggtacgcc     1080
tacgccgcct ccacgagtt ctacgacggc cgctacggca tgggtacggc gcgcagcgaa     1140
gaaggcccgc tggtgttcac cacccactcc acccacaagc tgctggcggc cttcagtcag   1200
gcctcgatga tccatgtgca ggacggcgg gccccgcagc tggaccggga tcgcttcaac     1260
gaggcgttca tgatgcacat ctccacttcg ccccagtacg gcatcatcgc ctcgctggac   1320
gtcgcctcgg cgatgatgga aggccccgcc gggcgctcgc tgatccagga aaccttcgac  1380
gaggccctga gcttccgccg tgccctggcc aacgtctggc agaccctgga tgccaaggat   1440
tggtggttcg atatctggga gccgcccag gtggaaggcg ccgaggcggt ggccaccggc    1500
gactgggtgc tggagcccgg cgccgactgg cacggcttcg cgaggtggc ggacgactac     1560
gtgctgctcg acccgatcaa ggtcaccctg gtcaccccg gctcagtgc cgacggcaag    1620
ctcggcgagc agggcatccc ggcggcggtg gtgggcaagt tcctctggga gcgtggcctg    1680
gtggtggaga gaccggtct ctactccttc ctcgtgctgt tctccatggg catcaccaag     1740
ggcaaatgga gcaccctgct caccgagctg ctggagttca aacgctccta cgacgccaac   1800
gccccgctga ccagtgcact gccctcggtg gcccgggccg atgccgcccg ctaccagggg    1860
ctgggcctgc cgacctctg cgaccagctg cacgcctgct accgcgacaa cgccacggcc    1920
aaggccatgc ggcgcatgta caccgcgctt ccggagctgg ccatcaagcc gtcggaggct   1980
tacgacaagc tggtgcgtgg cgaggtcgag gcggtgccca tcgagcagct gcaagggcgc    2040
attgccgcgg tgatgctggt gccgtacccg ccgggcatcc cgctgatcat gccggggag     2100
cgtttcactg cgcagacccg ctcgatcatt gactacctgg ccttcgcccg gaccttcgac   2160
agcgccttcc ccggcttcga ttccgatgtc cacggcctgc agcacgacga cagcccaatg  2220
gggcgctgct ataccgttga ttgcataagg gagtga                             2256
```

<210> SEQ ID NO 5
<211> LENGTH: 751
<212> TYPE: PRT
<213> ORGANISM: Pseudomonas resinovorans
<220> FEATURE:
<221> NAME/KEY: PEPTIDE
<222> LOCATION: (1)..(751)
<223> OTHER INFORMATION: Lysine decarboxylase from Pseudomonas
      resinovorans (PrLDC)

<400> SEQUENCE: 5

```
Met Tyr Lys Glu Leu Lys Phe Pro Val Leu Ile Val His Arg Asp Ile
  1               5                  10                  15

Lys Ala Asp Thr Val Ala Gly Glu Arg Val Arg Ser Ile Ala Arg Glu
                 20                  25                  30

Leu Glu Gln Asp Gly Phe Thr Ile Leu Pro Thr Ala Ser Ser Ala Glu
             35                  40                  45

Gly Arg Ile Val Ala Ser Thr His His Gly Leu Ala Cys Ile Leu Val
         50                  55                  60

Ala Ala Glu Gly Ala Gly Glu Asn Gln Arg Leu Leu Gln Asp Met Val
 65                  70                  75                  80

Glu Leu Ile Arg Val Ala Arg Val Arg Ala Pro Gln Leu Pro Ile Phe
                 85                  90                  95

Ala Leu Gly Glu Gln Val Thr Ile Glu Asn Ala Pro Ala Glu Ala Met
            100                 105                 110

Ala Asp Leu Asn Gln Leu Arg Gly Leu Leu Tyr Leu Tyr Glu Asp Thr
        115                 120                 125

Val Pro Phe Leu Ala Arg Gln Val Ala Arg Ala Arg Gly Tyr Leu
    130                 135                 140

Glu Ala Leu Leu Pro Pro Phe Phe Arg Ala Leu Val Glu His Thr Ala
145                 150                 155                 160

Gln Ser Asn Tyr Ser Trp His Thr Pro Gly His Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Ala Arg Ala Ala
    210                 215                 220

Gln Asn Phe Gly Ala Asp His Thr Phe Phe Val Ile Asn Gly Thr Ser
225                 230                 235                 240

Thr Ala Asn Lys Ile Val Trp His Ser Met Val Gly Arg Asp Asp Leu
                245                 250                 255

Val Leu Val Asp Arg Asn Cys His Lys Ser Ile Val His Ser Ile Ile
            260                 265                 270

Met Thr Gly Ala Ile Pro Leu Tyr Leu Thr Pro Glu Arg Asn Glu Leu
        275                 280                 285

Gly Ile Ile Gly Pro Ile Pro Leu Ala Glu Phe Ser Arg Glu Ser Ile
    290                 295                 300

Gln Ala Lys Ile Asp Ala Ser Pro Leu Ala Lys Gly Arg Ala Ala Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Ala Leu Gly Asp Ser Val Glu Val Leu
            340                 345                 350

His Phe Asp Glu Ala Trp Tyr Ala Tyr Ala Ala Phe His Glu Phe Tyr
        355                 360                 365

Ala Gly Arg Tyr Gly Met Cys Thr His Arg Glu Ala His Ser Pro Leu
    370                 375                 380

Val Phe Thr Thr His Ser Thr His Lys Leu Leu Ala Ala Phe Ser Gln
385                 390                 395                 400

Ala Ser Met Ile His Val Gln Asp Gly Gly Ala Arg Gln Leu Asp Arg
```

His Arg Phe Asn Glu Ala Phe Met Met His Ile Ser Thr Ser Pro Gln
            405                 410                 415

Tyr Gly Ile Ile Ala Ser Leu Asp Val Ala Ser Ala Met Met Glu Gly
        420                 425                 430

Pro Ala Gly Arg Ser Leu Ile Gln Glu Thr Phe Asp Glu Ala Leu Arg
    435                 440                 445

Phe Arg Arg Ala Leu Ala Asn Leu Arg Gln Asn Leu Ala Ala Asp Asp
450                 455                 460

Trp Trp Phe Asp Ile Trp Gln Ser His Leu Ala Glu Gly Ala Asp Thr
465                 470                 475                 480

Val Ala Thr Glu Asp Trp Leu Leu Arg Pro Asp Ala Asp Trp His Gly
            485                 490                 495

Phe Gly Asp Val Ala Glu Asp Tyr Val Leu Leu Asp Pro Ile Lys Val
        500                 505                 510

Thr Leu Val Thr Pro Gly Leu Thr Ala Asp Gly Lys Leu Gly Glu Arg
    515                 520                 525

Gly Ile Pro Ala Ala Val Val Ser Lys Phe Leu Trp Glu Arg Gly Val
530                 535                 540

Val Val Glu Lys Thr Gly Leu Tyr Ser Phe Leu Val Leu Phe Ser Met
545                 550                 555                 560

Gly Ile Thr Lys Gly Lys Trp Ser Thr Leu Leu Thr Glu Leu Leu Glu
            565                 570                 575

Phe Lys Arg Gly Tyr Asp Thr Asn Leu Pro Leu Ala Glu Ala Leu Pro
        580                 585                 590

Ser Ile Ala Arg Asp His Gly Ala Arg Tyr Ala Gly Met Gly Leu Arg
    595                 600                 605

Asp Leu Cys Asp Ala Leu His Gly Cys Tyr Arg Asn Ser Ala Thr Pro
610                 615                 620

Lys Ala Leu Arg Arg Met Tyr Thr Gln Leu Pro Glu Leu Ala Met Lys
625                 630                 635                 640

Pro Ala Asp Ala Tyr Asp Lys Leu Val Arg Gly Glu Val Glu Pro Val
            645                 650                 655

Ser Leu Asp Leu Leu Gln Gly Arg Ile Ala Ala Val Met Leu Val Pro
        660                 665                 670

Tyr Pro Pro Gly Ile Pro Leu Ile Met Pro Gly Glu Arg Phe Thr Ala
    675                 680                 685

Glu Thr Arg Ala Ile Ile Asp Tyr Leu Glu Phe Ala Arg Thr Phe Asp
690                 695                 700

Leu Ser Phe Pro Gly Phe Asp Ile Asp Val His Gly Leu Asn Cys Gln
705                 710                 715                 720

Glu Ser Pro Thr Gly Arg Cys Tyr Thr Val Asp Cys Ile Arg Glu
            725                 730                 735

740                 745                 750

<210> SEQ ID NO 6
<211> LENGTH: 2256
<212> TYPE: DNA
<213> ORGANISM: Pseudomonas resinovorans
<220> FEATURE:
<221> NAME/KEY: gene
<222> LOCATION: (1)..(2256)
<223> OTHER INFORMATION: Lysine decarboxylase gene from Pseudomonas
      resinovorans (prldc)

<400> SEQUENCE: 6
atgtacaaag agctcaagtt ccccgtcctc atcgtccatc gtgacatcaa ggccgatacc     60

```
gtcgccggcg agcgggtccg cagcatcgcc cgcgagctgg agcaggacgg cttcaccatc      120
ctccccaccg ccagctccgc cgaaggccgt atcgtcgcct ccacccacca tggcctcgcc      180
tgcatcctgg tggccgccga aggcgccggg gaaaaccagc ggctgctgca ggacatggtg      240
gagctgatcc gcgtggcgcg ggtgcgcgcg ccgcagttgc cgatcttcgc cctgggggaa      300
caggtcacca tcgagaacgc gccggccgag gccatggccg acctcaacca gttgcgcggc      360
ctgctctatc tctacgaaga caccgtgcct ttcctcgccc gccaggtggc ccgagccgcc      420
cgcggctacc tggaagccct gttgccgcca ttcttccgcg ccctggtcga gcacaccgcg      480
cagtccaact actcctggca caccccgggc acggcggtg gcgtggccta ccgcaagagt       540
ccggtggggc aggccttcca ccagttcttc ggggaaaaca ccctgcgctc ggacctctcg      600
gtatcggtgc cggaactggg ctcgctgctg accacaccg ggcccctggc cgaagccgag       660
gcgcgtgcgg cgcagaactt cggcgccgac acaccttct tcgtgatcaa tggcacttcc       720
accgccaaca gatcgtctg gcactccatg gtcggccgcg atgacctggt gctggtggac       780
cgcaactgcc acaagtccat cgtccactcg atcatcatga ccggcgccat ccccctgtac      840
ctgacgccgg agcgcaacga actgggcatc atcggaccca tcccccctcgc cgaattcagc    900 cgtgagtcga tccaggcgaa gatcgacgcc agccccctgg ccaaggggcg agccgccaag      960
gtcaagctgg cggtggtgac caactccacc tacgacggcc tctgctacaa cgccgagctg     1020
atcaagcagg cactgggcga ctcggtggag gtgctgcact cgacgaggc ctggtacgcc      1080 tacgctgcct tccacgagtt ctatgccggg cgctacggca tgtgcaccca ccgcgaggcg     1140
cactcgccgc tggtcttcac cacccattcc acccacaagc tgctggccgc cttcagccag     1200
gcctcgatga tccatgtgca ggacggcggc gcgcgccagc tcgaccggca ccgcttcaac     1260
gaagccttca tgatgcacat ctccacctcg ccgcagtacg catcatcgc ttccctggac      1320 gtggcctcgg ccatgatgga ggggcccgcc gggcgctcgt tgatccagga cttcgac       1380 gaggcgctgc gttttcgccg cgccctggcc aacctgcggc agaacctggc ggcggacgac     1440
tggtggttcg atatctggca gtcgcacctg gcggaaggcg ccgacacggt cgccaccgag     1500
gattggctgt tgcgtcccga cgccgactgg cacggattcg gcgatgtggc cgaggactac     1560
gtgctgctcg atccgatcaa ggtcacccctg gtgacgccgg gcctgaccgc cgatggcaag    1620
ctgggggagc ggggcattcc cgcggcgtg tcagcaagt tcctctggga gcgtggggtg       1680
gtggtggaga gaccggcct ctattccttc ctggtgctgt tctccatggg tatcaccaag      1740
ggcaagtgga gcaccctgct caccgagttg ctggagttca gcgcggcta tgacaccaac      1800 ctgccgctgg ccgaggcgct gccctccatc gccccgggacc acggcgcgcg gtacgccggc    1860
atgggcctgc gcgatctctg cgacgccctg catggctgct accgcaacag cgccacgccc    1920
aaggccctgc ggcgcatgta cacacagctg ccggaactgg cgatgaagcc cgccgacgct    1980
tacgacaagc tggtgcgcgg cgaggtggaa ccggtgtccc tggacctgct gcaagggcg     2040 atcgcggcgg tgatgctggt gccctatcca ccggcatac cgctgatcat gccggggag     2100 cgcttcaccg ccgagactcg cgcgatcatc gattacctgg aattcgcccg caccttcgac   2160
ctgagcttcc ccgccttcga tatcgatgtg catggcctca actgtcagga aagtcctacc   2220
gggcgctgct atacagtgga ctgcatcagg gaataa                              2256

<210> SEQ ID NO 7
<211> LENGTH: 749
<212> TYPE: PRT
```

```
<213> ORGANISM: Pseudomonas putida
<220> FEATURE:
<221> NAME/KEY: PEPTIDE
<222> LOCATION: (1)..(749)
<223> OTHER INFORMATION: Lysine decarboxylase from Pseudomonas putida
      (PpLDC)

<400> SEQUENCE: 7
```

| | | | | | | | | | | | | | | |
|---|---|---|---|---|---|---|---|---|---|---|---|---|---|---|
| Met | Tyr | Lys | Asp | Leu | Lys | Phe | Pro | Ile | Leu | Ile | Val | His | Arg | Ala | Ile |
| 1 | | | | 5 | | | | | 10 | | | | | 15 | |
| Lys | Ala | Asp | Ser | Val | Ala | Gly | Glu | Arg | Val | Arg | Gly | Ile | Ala | Glu | Glu |
| | | | 20 | | | | | 25 | | | | | 30 | | |
| Leu | Arg | Gln | Asp | Gly | Phe | Ala | Ile | Leu | Ala | Ala | Asp | His | Ala | Glu | |
| | | 35 | | | | | 40 | | | | | 45 | | | |
| Ala | Arg | Leu | Val | Ala | Ala | Thr | His | His | Gly | Leu | Ala | Cys | Met | Leu | Ile |
| | 50 | | | | | 55 | | | | | 60 | | | | |
| Ala | Ala | Glu | Gly | Val | Gly | Glu | Asn | Thr | His | Leu | Leu | Gln | Asn | Met | Ala |
| 65 | | | | 70 | | | | | 75 | | | | | 80 | |
| Glu | Leu | Ile | Arg | Leu | Ala | Arg | Leu | Arg | Ala | Pro | Asp | Leu | Pro | Ile | Phe |
| | | | 85 | | | | | 90 | | | | | 95 | | |
| Ala | Leu | Gly | Glu | Gln | Val | Thr | Leu | Glu | Asn | Ala | Pro | Ala | Glu | Ala | Met |
| | | | 100 | | | | | 105 | | | | | 110 | | |
| Ser | Glu | Leu | Asn | Gln | Leu | Arg | Gly | Ile | Leu | Tyr | Leu | Phe | Glu | Asp | Thr |
| | | | 115 | | | | | 120 | | | | | 125 | | |
| Val | Pro | Phe | Leu | Ala | Arg | Gln | Val | Ala | Arg | Ala | Ala | His | Thr | Tyr | Leu |
| | 130 | | | | | 135 | | | | | 140 | | | | |
| Asp | Gly | Leu | Leu | Pro | Pro | Phe | Phe | Lys | Ala | Leu | Val | Gln | His | Thr | Ala |
| 145 | | | | | 150 | | | | | 155 | | | | | 160 |
| Gln | Ser | Asn | Tyr | Ser | Trp | His | Thr | Pro | Gly | His | Gly | Gly | Val | Ala | |
| | | | | 165 | | | | | 170 | | | | | 175 | |
| Tyr | His | Lys | Ser | Pro | Val | Gly | Gln | Ala | Phe | His | Gln | Phe | Phe | Gly | Glu |
| | | | 180 | | | | | 185 | | | | | 190 | | |
| Asn | Thr | Leu | Arg | Ser | Asp | Leu | Ser | Val | Ser | Val | Pro | Glu | Leu | Gly | Ser |
| | | | 195 | | | | | 200 | | | | | 205 | | |
| Leu | Leu | Asp | His | Thr | Gly | Pro | Leu | Ala | Glu | Ala | Glu | Ala | Arg | Ala | Ala |
| | | 210 | | | | | 215 | | | | | 220 | | | |
| Arg | Asn | Phe | Gly | Ala | Asp | His | Thr | Phe | Phe | Val | Ile | Asn | Gly | Thr | Ser |
| 225 | | | | | 230 | | | | | 235 | | | | | 240 |
| Thr | Ala | Asn | Lys | Ile | Val | Trp | His | Ala | Met | Val | Gly | Arg | Asp | Asp | Leu |
| | | | 245 | | | | | 250 | | | | | 255 | | |
| Val | Leu | Val | Asp | Arg | Asn | Cys | His | Lys | Ser | Val | His | Ala | Ile | Ile | |
| | | 260 | | | | | 265 | | | | | 270 | | | |
| Met | Thr | Gly | Ala | Val | Pro | Leu | Tyr | Leu | Cys | Pro | Glu | Arg | Asn | Glu | Leu |
| | | 275 | | | | | 280 | | | | | 285 | | | |
| Gly | Ile | Ile | Gly | Pro | Ile | Pro | Leu | Ser | Glu | Phe | Ser | Pro | Glu | Ala | Ile |
| | | 290 | | | | | 295 | | | | | 300 | | | |
| Glu | Ala | Lys | Ile | Gln | Ala | Asn | Pro | Leu | Ala | Arg | Asp | Arg | Gly | Arg | Arg |
| 305 | | | | | 310 | | | | | 315 | | | | | 320 |
| Ile | Lys | Leu | Ala | Val | Val | Thr | Asn | Ser | Thr | Tyr | Asp | Gly | Leu | Cys | Tyr |
| | | | | 325 | | | | | 330 | | | | | 335 | |
| His | Ala | Gly | Met | Ile | Lys | Gln | Cys | Leu | Gly | Ala | Ser | Val | Glu | Val | Leu |
| | | | 340 | | | | | 345 | | | | | 350 | | |
| His | Phe | Asp | Glu | Ala | Trp | Phe | Ala | Tyr | Ala | Ala | Phe | His | Asp | Phe | Phe |
| | | | 355 | | | | | 360 | | | | | 365 | | |
| Thr | Gly | Arg | Tyr | Ala | Met | Gly | Thr | Ala | Cys | Thr | Ala | Gly | Ser | Pro | Leu |

```
            370                 375                 380
Val Phe Ser Thr His Ser Thr His Lys Leu Leu Ala Ala Phe Ser Gln
385                 390                 395                 400

Ala Ser Met Ile His Val Gln Asp Gly Ala Arg Arg Gln Leu Asp Arg
                405                 410                 415

Asp Arg Phe Asn Glu Ala Phe Met Met His Ile Ser Thr Ser Pro Gln
                420                 425                 430

Tyr Ser Ile Leu Ala Ser Leu Asp Val Ala Ser Ser Met Met Glu Gly
                435                 440                 445

Pro Ala Gly His Ser Leu Leu Gln Glu Met Phe Asp Glu Ala Leu Ser
            450                 455                 460

Phe Arg Arg Ala Leu Ala Asn Leu Arg Glu His Ile Ala Ala Asp Asp
465                 470                 475                 480

Trp Trp Phe Ser Ile Trp Gln Pro Pro Gly Thr Glu Gly Ile Gln Arg
                485                 490                 495

Leu Ala Ala Gln Asp Trp Leu Leu Gln Pro Gly Ala Glu Trp His Gly
                500                 505                 510

Phe Gly Glu Val Val Asp Asp Tyr Val Leu Leu Asp Pro Leu Lys Val
                515                 520                 525

Thr Leu Val Met Pro Gly Leu Ser Ala Gly Gly Val Leu Gly Glu His
            530                 535                 540

Gly Ile Pro Ala Ala Val Val Ser Lys Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Leu Thr Glu Leu Leu Glu
                580                 585                 590

Phe Lys Arg His Tyr Asp Gly Asn Thr Ala Leu Ser Ser Cys Leu Pro
                595                 600                 605

Ser Val Val Ala Ala Asp Ala Ser Arg Tyr Gln Arg Met Gly Leu Arg
            610                 615                 620

Asp Leu Cys Asp Gln Leu His Asp Cys Tyr Arg Ala Asn Ala Thr Ala
625                 630                 635                 640

Lys Gln Leu Lys Arg Leu Phe Thr Arg Leu Pro Glu Val Ala Val Ser
                645                 650                 655

Pro Ala Arg Ala Tyr Asp Gln Met Val Arg Gly Asp Val Glu Ala Val
                660                 665                 670

Pro Ile Glu Ala Leu Leu Gly Arg Val Ala Val Met Leu Val Pro
                675                 680                 685

Tyr Pro Pro Gly Ile Pro Leu Ile Met Pro Gly Glu Arg Phe Thr Glu
            690                 695                 700

Ala Thr Arg Ser Ile Leu Asp Tyr Leu Ala Phe Ala Arg Ala Phe Asn
705                 710                 715                 720

Gln Gly Phe Pro Gly Phe Val Ala Asp Val His Gly Leu Gln Asn Glu
                725                 730                 735

Ser Gly Arg Tyr Thr Val Asp Cys Ile Thr Glu Cys Glu
            740                 745
```

<210> SEQ ID NO 8
<211> LENGTH: 2250
<212> TYPE: DNA
<213> ORGANISM: Pseudomonas putida
<220> FEATURE:
<221> NAME/KEY: gene
<222> LOCATION: (1)..(2250)

<223> OTHER INFORMATION: Lysine decarboxylase gene from Pseudomonas putida (ppldc)

<400> SEQUENCE: 8

```
atgtacaagg acctcaagtt cccgatcctc atcgtccacc gggctatcaa ggctgacagt      60
gtcgccgggg agcgcgtgcg gggcatcgcc gaggaactgc gccaggacgg tttcgccatt     120
ctggccgccg ccgaccacgc cgaagcgcgc ctggttgccg ccactcacca cggcctggcc     180
tgcatgctga ttgccgccga aggagttggc gaaaacaccc acctgctgca gaacatggcc     240
gagctgatcc gcctggcgcg catgcgcgcg cccgacttgc cgatcttcgc cttgggcgag     300
caggtgaccc tggaaaacgc ccctgccgaa gccatgagcg agctcaacca actgcgtggc     360
atcctttacc tgttcgaaga caccgtgccg tttctcgccc gccaggtggc gcgtgccgca     420
cacacctacc ttgacggtct gctgccaccg ttcttcaagg ccctggtgca gcataccgcg     480
cagtccaact attcctggca taccccgggc catggcggtg gcgtggccta tcataaaagc     540
ccggtaggcc aggccttcca ccagttcttc ggggaaaaca ccctgcgctc ggacctgtct     600
gtttcagtgc cggagctggg ctcgctgctc gaccacacag gccccttggc cgaagccgag     660
gccagggcgg cgcgcaactt cggtgccgac acacccttct tcgtcatcaa tggcacctcc     720
acagccaaca agattgtctg gcacgccatg gtcggtcgcg acgacctggt gttggtggac     780
cgcaactgcc ataagtcagt ggtgcacgcg atcatcatga ccggcgccat tccgctgtac     840
ctgtgcccag agcgcaacga gctgggcatc atcggcccga tcccgctcag cgagttcagc     900
cccgaggcaa tcgaggcgaa gatccaggcc aaccccccttg cccatggccg tgggcaacgt     960
atcaagctgg cggtagtgac caactccacc tatgacgggc tgtgctacca cgccgggatg    1020
atcaagcagg ccctgggtgc cagcgtggaa gtactgcact cgacgaggc ctggttcgct    1080
tatgcggcgt ttcacggctt cttcaccggg cgctatgcca tgggcactgc ctgcgcagcc    1140
gacagcccgt tggtgttcag cacccattcc acccacaagc tgctggcggc gttcagccag    1200
gcctcgatga tccatgtgca ggacgggcc aggcggcagc tggaccggga ccgcttcaac    1260
gaagcgttca tgatgcatat ctcgacttcg ccgcagtaca gcatccttgc ctcgctggac    1320
gtggcctcga ccatgatgga agggcaggcc gggcattcgc tgttgcaaga aatgttcgat    1380
gaggcgctga gttttcgtcg tgccctggcc aacctgcgcg agcacattgc tgcggatgac    1440
tggtggttca gtatttggca gccgcccagc actgaaggca tccagccctt ggccgcgcag    1500
gactggctgc tgcagccggg ggcgcagtgg catggctttg tgaggtggc ggacggctac    1560
gtgttgctcg accctctgaa ggtgaccctg gtaatgccgg gctgagtgc gggcggtgtg    1620
ctgggtgagc gtggcatccc ggcggcggtg gtcagcaagt ttctctggga gcgcgggctg    1680
gtggtggaaa aaccggcttt gtacagcttc tggtgctgt tttccatggg catcaccaag    1740
ggcaagtgga gcaccttgct caccgaactg ctggagttca gcgccacta tgacggcaat    1800
acaccgctga gcagttgcct gccgagtgtg ggggttgccg atgcctcacg ctaccggggc    1860
atgggcctgc gcgacctgtg tgaacagttg catgactgct accgtgccaa tgccacggcc    1920
aagcagctga gcgggtgttt cacgcgtttg ccggaggtgg ccgtgagccc cgctcgggct    1980
tatgaccaga tggtacgtgg cgaggtgaa gcggtgccga tcgaagcttt gctgggccgt    2040
gtggccgcgg tgatgctggt gccgtacccg cccggtattc cgttgatcat gccgggagag    2100
cggttcaccg aggcgacccg ctcgatactg gactacttgg ccttcgcccg agccttcaac    2160
caaggctttc cggggtttgt cgcggatgtt cacggcctgc agaacgaaaa tggccgctac    2220
```
accgtggatt gcatcatgga atgcgagtga                                    2250

<210> SEQ ID NO 9
<211> LENGTH: 751
<212> TYPE: PRT
<213> ORGANISM: Pseudomonas synxantha
<220> FEATURE:
<221> NAME/KEY: PEPTIDE
<222> LOCATION: (1)..(751)
<223> OTHER INFORMATION: Lysine decarboxylase from Pseudomonas synxantha
    (PxLDC)

<400> SEQUENCE: 9

Met Tyr Lys Asp Leu Lys Phe Pro Ile Leu Ile Val His Arg Asp Ile
 1               5                  10                  15

Lys Ala Asp Thr Val Ala Gly Asp Arg Val Arg Gly Ile Ala Arg Glu
             20                  25                  30

Leu Glu Gln Glu Gly Phe Ser Ile Phe Ser Ala Val Asp Tyr Ala Glu
         35                  40                  45

Gly Arg Leu Val Ala Ser Thr His His Gly Leu Ala Cys Met Leu Ile
     50                  55                  60

Ala Ala Glu Gly Ala Gly Glu Asn Thr His Leu Leu Gln Asn Met Val
 65                  70                  75                  80

Glu Leu Ile Arg Leu Ala Arg Val Arg Ala Pro Asn Leu Pro Ile Phe
                 85                  90                  95

Ala Leu Gly Glu Gln Val Thr Leu Glu Asn Ala Pro Ala Asp Ala Met
            100                 105                 110

Ser Glu Leu Asn Gln Leu Arg Gly Ile Leu Tyr Leu Phe Glu Asp Thr
        115                 120                 125

Val Pro Phe Leu Ala Arg Gln Val Ala Arg Ser Ala Arg Thr Tyr Leu
    130                 135                 140

Asp Gly Leu Leu Pro Pro Phe Phe Lys Ala Leu Val Gln His Thr Ala
145                 150                 155                 160

Asp Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Ala Arg Ala Ala
    210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Asp Asp Leu
                245                 250                 255

Val Leu Val Asp Arg Asn Cys His Lys Ser Val Leu His Ser Ile Ile
            260                 265                 270

Met Thr Gly Ala Ile Pro Leu Tyr Leu Cys Pro Glu Arg Asn Glu Leu
        275                 280                 285

Gly Ile Ile Gly Pro Ile Pro Leu Ser Glu Phe Ser Pro Glu Ser Ile
    290                 295                 300

Arg Ala Lys Ile Asp Ala Ser Pro Leu Ala Tyr Gly Arg Pro Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Gln Leu Gly Asn Ser Val Glu Val Leu

His Phe Asp Glu Ala Trp Tyr Ala Tyr Ala Ala Phe His Glu Phe Phe
     355                 360                 365

Ala Gly Arg Tyr Gly Met Gly Thr Ser Arg Thr Pro Asp Ser Pro Leu
     370                 375                 380

Val Phe Thr Thr His Ser Thr His Lys Leu Leu Ala Ala Phe Ser Gln
385                 390                 395                 400

Ala Ser Met Ile His Val Gln Asp Gly Ala Arg Gln Leu Asp Arg
             405                 410                 415

Asp Arg Phe Asn Glu Ala Phe Met Met His Ile Ser Thr Ser Pro Gln
             420                 425                 430

Tyr Ser Ile Ile Ala Ser Leu Asp Val Ala Ser Ala Met Met Glu Gly
             435                 440                 445

Pro Ala Gly Arg Ser Leu Leu Gln Glu Met Phe Asp Glu Ala Leu Ser
             450                 455                 460

Phe Arg Arg Ala Leu Ala Asn Leu Arg Gln His Ile Ala Ala Glu Asp
465                 470                 475                 480

Trp Trp Phe Ser Ile Trp Gln Pro Gln Ser Val Ala Gly Ile Asp Arg
                 485                 490                 495

Val Ala Thr Ala Asp Trp Leu Leu His Pro Gln Asp Asp Trp His Gly
             500                 505                 510

Phe Gly Asp Val Ala Glu Asp Tyr Val Leu Leu Asp Pro Ile Lys Val
             515                 520                 525

Thr Leu Val Met Pro Gly Leu Asn Ala Gly Gly Ala Leu Ser Asp Cys
     530                 535                 540

Gly Ile Pro Ala Ala Val Ser Lys Phe Leu Trp Glu Arg Gly Leu
545                 550                 555                 560

Val Val Glu Lys Thr Gly Leu Tyr Ser Phe Leu Val Leu Phe Ser Met
                 565                 570                 575

Gly Ile Thr Lys Gly Lys Trp Ser Thr Leu Leu Thr Glu Leu Leu Glu
             580                 585                 590

Phe Lys Arg Ser Tyr Asp Ala Asn Val Ser Leu Ala Ser Cys Leu Pro
             595                 600                 605

Ser Val Tyr Ala Gln Gly Pro Val Arg Tyr Gln Gly Leu Gly Leu Arg
     610                 615                 620

Asp Leu Cys Asp Gln Leu His Ser Cys Tyr Arg Ser Asn Ala Thr Ala
625                 630                 635                 640

Lys His Leu Lys Arg Met Tyr Thr Val Leu Pro Gln Ile Ala Met Lys
                 645                 650                 655

Pro Ala Asp Ala Tyr Asp Gln Leu Val Arg Gly Glu Val Glu Ala Val
             660                 665                 670

Ser Ile Asp Ala Leu Pro Gly Arg Ile Ala Ala Val Met Leu Val Pro
     675                 680                 685

Tyr Pro Pro Gly Ile Pro Leu Ile Met Pro Gly Glu Arg Phe Thr Glu
     690                 695                 700

Ser Thr Arg Ser Ile Ile Asp Tyr Leu Ala Phe Ala Arg Thr Phe Asp
705                 710                 715                 720

Ser Ser Phe Pro Gly Phe Val Ala Asp Val His Gly Leu Gln His Glu
             725                 730                 735

Asp Asp Gly Ser Gly Arg Arg Tyr Thr Val Asp Cys Ile Lys Gly
             740                 745                 750

<210> SEQ ID NO 10
<211> LENGTH: 2256
<212> TYPE: DNA
<213> ORGANISM: Pseudomonas synxantha
<220> FEATURE:
<221> NAME/KEY: gene
<222> LOCATION: (1)..(2256)
<223> OTHER INFORMATION: Lysine decarboxylase gene from Pseudomonas synxantha (pxldc)

<400> SEQUENCE: 10

| | | | | | |
|---|---|---|---|---|---|
| atgtacaaag | acctcaagtt | ccctattctt | atcgtgcacc | gtgacatcaa | ggccgacacc | 60 |
| gttgccggtg | accgggttcg | aggcatcgcc | agggagttgg | aacaagaggg | cttcagtata | 120 |
| ttttctgcgg | tggattacgc | cgaagggcgg | ttggtggcct | ccacccatca | tggtttggcg | 180 |
| tgcatgttga | tcgcagcaga | aggcgccggg | gaaaataccc | acctgctgca | aaacatggtc | 240 |
| gagctgatcc | gcctggcgcg | ggtaagggca | cccaacctgc | cgatctttgc | cctgggtgag | 300 |
| caagtcaccc | ttgaaaacgc | gccggccgat | gcgatgagca | gcttaaacca | gctacgcggc | 360 |
| attctttatc | tgttcgaaga | caccgtgccg | ttcctggcgc | gccaggtcgc | ccgctctgcc | 420 |
| cgcacttacc | tggacggcct | gttaccgccg | ttcttcaagg | ccttggtgca | gcacaccgcc | 480 |
| gattccaatt | attcctggca | caccctggc | catggcggtg | gcgtggcgta | tcgtaaaagc | 540 |
| ccggtggggc | aggcgtttca | ccagttcttc | ggggagaaca | ccctgcgctc | ggacttgtct | 600 |
| gtttctgtcc | ctgaactggg | ctcgctgctc | gatcataccg | gcccctggc | cgaagccgag | 660 |
| gcccgcgccg | cgcgcaactt | tggcgccgac | catacctcct | tcgtcatcaa | tggcacctcc | 720 |
| accgccaaca | gatcgtctg | gcattccatg | gtcggtcgcg | acgacctggt | gttggtggac | 780 |
| cgcaactgcc | acaagtcagt | gctgcactcg | atcatcatga | ccggcgcgat | cccgctgtat | 840 |
| ctgtgcccgg | agcgcaacga | actggggatc | atcggcccga | tccccttgag | tgaattcagc | 900 |
| cccgaatcaa | tccgcgccaa | gatcgacgcc | agccgttgg | catatggccg | gccacccaag | 960 |
| gtgaagctgg | cggtggtgac | caattccacc | tacgacggcc | tgtgctacaa | cgccgaactg | 1020 |
| atcaagcagc | aattgggtaa | tagcgtagag | gtgctgcact | cgacgaagc | ctggtatgcc | 1080 |
| tatgcggcat | tcacgagtt | tttcgccggg | cgctatggca | tgggcacctc | gcgcacaccg | 1140 |
| gacagcccgc | tggtatttac | cacccactcc | acccacaaac | tgctggccgc | attcagccag | 1200 |
| gcatcgatga | ttcatgtgca | ggatggcggc | gcacggcagc | tggaccgtga | ccgtttcaac | 1260 |
| gaagccttca | tgatgcacat | ctcgacttca | ccgcaataca | gcatcatcgc | ttcgctggat | 1320 |
| gtcgcttcgg | cgatgatgga | aggccccgcc | gggcgctcgc | tgttgcagga | aatgttcgac | 1380 |
| gaggccctga | gtttccgccg | cgcgctggcc | aacctgcgcc | agcatatcgc | tgccgaggat | 1440 |
| tggtggtttt | cgatctggca | gccacaatcg | gtggcgggta | tcgaccgcgt | tgccacggcg | 1500 |
| gactggctat | tgcatcccca | ggatgattgg | cacggctttg | gcgatgtggc | tgaagattat | 1560 |
| gtcttgctgg | acccgatcaa | agtcaccctg | gtgatgcctg | gctcaatgc | aggtggcgcc | 1620 |
| ttgagcgatt | gtgggattcc | cgccgcggtg | gtcagcaagt | ttctctggga | gcgcggcctc | 1680 |
| gtggtggaaa | aaaccgggct | ttattcgttc | ctcgtgttgt | tttccatggg | gatcaccaaa | 1740 |
| ggcaagtgga | gcaccttgct | caccgagttg | ctggagttca | agcgcagtta | cgatgccaac | 1800 |
| gtcagcctgg | ccagttgttt | gccctcggtg | tacgcccagg | ggccggtacg | ttatcagggc | 1860 |
| ttgggcctgc | gcgatctttg | cgaccagttg | cacagctgtt | accgtagcaa | cgccaccgcc | 1920 |
| aagcatctca | agcgcatgta | cacagtattg | ccgcagatcg | cgatgaaacc | cgccgatgcc | 1980 |

```
tacgaccaac tggtcagagg cgaagttgaa gcggtatcca tcgatgcctt gccaggacgc    2040
atcgcagccg taatgctggt gccttatcca ccgggcattc cattgataat gcccggcgag    2100
cgctttactg aatcaacgcg ttcaatcatc gactacctgg catttgcccg cacgttcgat    2160
agcagtttcc ccggttttgt cgccgatgtt catgggctgc aacacgaaga tgatggcagt    2220
ggccgtcgtt acaccgtcga ttgcatcaag ggttaa                              2256
```

<210> SEQ ID NO 11
<211> LENGTH: 715
<212> TYPE: PRT
<213> ORGANISM: Escherichia coli
<220> FEATURE:
<221> NAME/KEY: PEPTIDE
<222> LOCATION: (1)..(715)
<223> OTHER INFORMATION: Lysine decarboxylase from Escherichia coli (EcLDC)

<400> SEQUENCE: 11

```
Met Asn Val Ile Ala Ile Leu Asn His Met Gly Val Tyr Phe Lys Glu
 1               5                  10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
```

```
            290                 295                 300
Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
                370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
                450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
                530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
                595                 600                 605

Ala Phe Glu Val Leu Pro Thr Met Val Met Thr Pro Tyr Ala Ala Phe
                610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
                675                 680                 685

Phe Glu Thr Asp Ile His Gly Ala Tyr Arg Gln Ala Asp Gly Arg Tyr
                690                 695                 700

Thr Val Lys Val Leu Lys Glu Glu Ser Lys Lys
705                 710                 715
```

```
<210> SEQ ID NO 12
<211> LENGTH: 31
<212> TYPE: PRT
<213> ORGANISM: Artificial Sequence
<220> FEATURE:
<223> OTHER INFORMATION: 15 amino acid of Lysine decarboxylase from
      Escherichia coli

<400> SEQUENCE: 12

Gly Arg Val Glu Gly Lys Val Ile Tyr Glu Thr Gln Ser Thr His Lys
 1               5                  10                  15

Leu Leu Ala Ala Phe Ser Gln Ala Ser Met Ile His Val Lys Gly
            20                  25                  30

<210> SEQ ID NO 13
<211> LENGTH: 33
<212> TYPE: DNA
<213> ORGANISM: Artificial Sequence
<220> FEATURE:
<223> OTHER INFORMATION: 5 LDC NdeI

<400> SEQUENCE: 13
aatatacata tgtacaaaga cctccaattc ccc                            33

<210> SEQ ID NO 14
<211> LENGTH: 35
<212> TYPE: DNA
<213> ORGANISM: Artificial Sequence
<220> FEATURE:
<223> OTHER INFORMATION: 3 LDC XhoI

<400> SEQUENCE: 14
aatatactcg agtcagatct tgatgcagtc caccg                          35

<210> SEQ ID NO 15
<211> LENGTH: 34
<212> TYPE: DNA
<213> ORGANISM: Artificial Sequence
<220> FEATURE:
<223> OTHER INFORMATION: 5 LDC BamHI

<400> SEQUENCE: 15
aatataggat ccgtacaaag acctccaatt cccc                           34

<210> SEQ ID NO 16
<211> LENGTH: 35
<212> TYPE: DNA
<213> ORGANISM: Artificial Sequence
<220> FEATURE:
<223> OTHER INFORMATION: 3 LDC SacI

<400> SEQUENCE: 16
aatatagagc tctcagatct tgatgcagtc caccg                          35

<210> SEQ ID NO 17
<211> LENGTH: 37
<212> TYPE: DNA
<213> ORGANISM: Artificial Sequence
<220> FEATURE:
<223> OTHER INFORMATION: 5 PaLDC NdeI

<400> SEQUENCE: 17
aatatacata tgtacaaaga cctgaagttc cccatcc                        37
```

```
<210> SEQ ID NO 18
<211> LENGTH: 41
<212> TYPE: DNA
<213> ORGANISM: Artificial Sequence
<220> FEATURE:
<223> OTHER INFORMATION: 3 PaLDC XhoI

<400> SEQUENCE: 18
aatatactcg agtcactccc ttatgcaatc aacggtatag c        41

<210> SEQ ID NO 19
<211> LENGTH: 39
<212> TYPE: DNA
<213> ORGANISM: Artificial Sequence
<220> FEATURE:
<223> OTHER INFORMATION: 5 PrLDC NdeI

<400> SEQUENCE: 19
aatatacata tgtacaaaga gctcaagttc cccgtcctc          39

<210> SEQ ID NO 20
<211> LENGTH: 41
<212> TYPE: DNA
<213> ORGANISM: Artificial Sequence
<220> FEATURE:
<223> OTHER INFORMATION: 3 PrLDC XhoI

<400> SEQUENCE: 20
aatatactcg agttattccc tgatgcagtc cactgtatag c        41

<210> SEQ ID NO 21
<211> LENGTH: 33
<212> TYPE: DNA
<213> ORGANISM: Artificial Sequence
<220> FEATURE:
<223> OTHER INFORMATION: 5_LDC_NdeI_ppldc

<400> SEQUENCE: 21
aatatacata tgtacaaaga cctccaattc ccc                33

<210> SEQ ID NO 22
<211> LENGTH: 41
<212> TYPE: DNA
<213> ORGANISM: Artificial Sequence
<220> FEATURE:
<223> OTHER INFORMATION: 3_PaLDC_XhoI_ppldc

<400> SEQUENCE: 22
aatatactcg agtcactccc ttatgcaatc aacggtatag c        41

<210> SEQ ID NO 23
<211> LENGTH: 33
<212> TYPE: DNA
<213> ORGANISM: Artificial Sequence
<220> FEATURE:
<223> OTHER INFORMATION: 5_LDC_NdeI_pxldc

<400> SEQUENCE: 23
aatatacata tgtacaaaga cctccaattc ccc                33

<210> SEQ ID NO 24
<211> LENGTH: 41
<212> TYPE: DNA
<213> ORGANISM: Artificial Sequence
<220> FEATURE:
<223> OTHER INFORMATION: 3_PaLDC_XhoI_pxldc
```

```
<400> SEQUENCE: 24
aatatactcg agtcactccc ttatgcaatc aacggtatag c                    41
```

US 10,351,839 B2

LYSINE DECARBOXYLASE HAVING IMPROVED STABILITY WITH A PH CHANGE, MICROORGANISM COMPRISING A POLYNUCLEOTIDE ENCODING THE SAME, AND METHOD FOR PRODUCING CADAVERINE USING THE SAME

TECHNICAL FIELD

The present invention relates to a novel lysine decarboxylase, a microorganism transformed with a gene encoding a protein having the corresponding activity, and a method of producing cadaverine by using the same.

BACKGROUND ART

A general method of producing nylon by using diamine is a chemical process of using 1,4-diaminobutane and hexamethylenediamine as raw materials. These raw materials are produced from petroleum-based organic compounds. Therefore, as environmental regulations are strengthened, market demand for alternative materials produced through bio-based routes is growing.

Meanwhile, cadaverine is a diamine organic compound composed of 5 carbons which has a molecular formula of $NH_2(CH_2)_5NH_2$, and it may be a raw material for nylon 5,6. If bio-based preparation of cadaverine is possible, it is expected that a variety of nylons can be produced while satisfying the market demand for bio-based materials.

Regarding bio-based production of cadaverine, studies on bioconversion of lysine were widely known before the 1940's (Gale E. F., Epps H. M. 1944. Studies on bacterial amino-acid decarboxylases. Biochem J. 38, 232-242). In a key stage of the bioconversion, lysine decarboxylase is an enzyme that produces cadaverine from lysine (FIG. 1). Activity of lysine decarboxylase in many different microorganisms has been reported, and lysine decarboxylase, of which specific activity (mmol/min/mg) is known, is derived from four kinds of microorganisms (*Escherichia coli, Bacterium cadaveris, Glycine max*, and *Selenomonas ruminantium*). Of them, lysine decarboxylase derived from *Escherichia coli* is evaluated as the lysine decarboxylase having the highest activity, and the enzyme used in practical production is also limited to CadA which is derived from *Escherichia coli* (Japanese Patent No. 2005-147171, European Patent No. 2004-010711, and Japanese Patent No. 2002-257374). However, production of cadaverine by reacting lysine with lysine decarboxylase generates carbon dioxide by decarboxylation of lysine, and produces a divalent cation, cadaverine from a monovalent cation, lysine thereby increasing pH during the reaction. Thus, when the enzymatic reaction of lysine decarboxylase occurs, pH is changed, which generates a problem of efficiency reduction. Further, the enzyme may be denatured by an acid produced in a reaction solution, or a base, thereby losing its activity.

Accordingly, the present inventors discovered a novel lysine decarboxylase having stability against high temperature and pH, and found that the lysine decarboxylase may be expressed in a microorganism belonging to *Escherichia* sp., thereby completing the present invention.

DETAILED DESCRIPTION OF THE INVENTION

Technical Problem

An object of the present invention is to provide a novel lysine decarboxylase and a polynucleotide encoding a protein having the corresponding activity.

Another object of the present invention is to provide a microorganism which is transformed to express the lysine decarboxylase.

Still another object of the present invention is to provide a method of producing cadaverine by using the enzyme or the microorganism including the same.

Technical Solution

In a specific aspect of the present invention, provided is a protein having novel lysine decarboxylase activity, including an amino acid sequence of SEQ ID NO: 1 or an amino acid sequence having 75% or more sequence homology therewith.

As used herein, the term "protein having the lysine decarboxylase activity" refers to a protein having activity of catalyzing a decarboxylation reaction of lysine using pyridoxal-5'-phosphate as a coenzyme to decarboxylate lysine, thereby producing cadaverine and carbon dioxide.

The protein having the lysine decarboxylase activity including the amino acid sequence of SEQ ID NO: 1 or the amino acid sequence having 75% or more sequence homology therewith may be a protein having lysine decarboxylase activity, which is newly discovered in a microorganism of *Pseudomonas* sp., and the protein may include all proteins, as long as they have the corresponding activity and are discovered in a microorganism of *Pseudomonas* sp. For example, the microorganism of *Pseudomonas* sp. may be *Pseudomonas thermotolerans, Pseudomonas alcaligenes, Pseudomonas resinovorans, Pseudomonas putida,* and *Pseudomonas synxantha*.

Specifically, a protein having novel lysine decarboxylase activity derived from the *Pseudomonas thermotolerans* microorganism may have an amino acid sequence of SEQ ID NO: 1 or an amino acid sequence having about 75% or more, about 80% or more, about 85% or more, about 90% or more, or about 95% or more sequence homology with SEQ ID NO: 1. A protein having lysine decarboxylase activity derived from the *Pseudomonas alcaligenes* microorganism may have an amino acid sequence of SEQ ID NO: 3 or an amino acid sequence having about 75% or more, about 80% or more, about 90% or more, or about 95% or more sequence homology with SEQ ID NO: 3. A protein having lysine decarboxylase activity derived from the *Pseudomonas resinovorans* microorganism may have an amino acid sequence of SEQ ID NO: 5 or an amino acid sequence having about 75% or more, about 80% or more, about 90% or more, or about 95% or more sequence homology with SEQ ID NO: 5. A protein having lysine decarboxylase activity derived from the *Pseudomonas putida* microorganism may have an amino acid sequence of SEQ ID NO: 7 or an amino acid sequence having about 75% or more, about 80% or more, about 90% or more, or about 95% or more sequence homology with SEQ ID NO: 7. A protein having lysine decarboxylase activity derived from the *Pseudomonas synxantha* microorganism may have an amino acid sequence of SEQ ID NO: 9 or an amino acid sequence having about 75% or more, about 80% or more, about 90% or more, or about 95% or more sequence homology with SEQ ID NO: 9. However, the proteins are not limited to the above amino acid sequences, and the proteins may have all amino acid sequences, as long as the amino acid sequences are able to maintain the lysine decarboxylase activity.

Further, in another specific aspect of the present invention, provided is a polynucleotide encoding the novel protein having the lysine decarboxylase activity, specifically, a polynucleotide having 75% or more sequence homology with a nucleotide sequence of SEQ ID NO: 2.

The nucleotide sequence encoding the protein having the lysine decarboxylase activity may be obtained from a known genomic sequence derived from the *Pseudomonas* sp. microorganism. Specifically, the nucleotide sequence may be obtained from genomic sequences derived from one or more microorganisms selected from the group consisting of *Pseudomonas thermotolerans, Pseudomonas alcaligenes, Pseudomonas resinovorans, Pseudomonas putida*, and *Pseudomonas synxantha*. A nucleotide sequence encoding the lysine decarboxylase which is derived from the *Pseudomonas thermotolerans* microorganism may have the nucleotide sequence of SEQ ID NO: 2, and also may have a nucleotide sequence having about 75% or more, about 80% or more, about 90% or more, or about 95% or more sequence homology with the nucleotide sequence of SEQ ID NO: 2. A nucleotide sequence encoding the lysine decarboxylase which is derived from the *Pseudomonas alcaligenes* microorganism may have a nucleotide sequence of SEQ ID NO: 4, and also may have a nucleotide sequence having about 75% or more, about 80% or more, about 90% or more, or about 95% or more sequence homology with the nucleotide sequence of SEQ ID NO: 4. A nucleotide sequence encoding the lysine decarboxylase which is derived from the *Pseudomonas resinovorans* microorganism may be obtained from a known genomic sequence of *Pseudomonas resinovorans*, and specifically, may have a nucleotide sequence of SEQ ID NO: 6, and also may have a nucleotide sequence having about 75% or more, about 80% or more, about 90% or more, or about 95% or more sequence homology with the nucleotide sequence of SEQ ID NO: 6. A nucleotide sequence encoding the lysine decarboxylase which is derived from the *Pseudomonas putida* microorganism may have a nucleotide sequence of SEQ ID NO: 8, and also may have a nucleotide sequence having about 75% or more, about 80% or more, about 90% or more, or about 95% or more sequence homology with the nucleotide sequence of SEQ ID NO: 8. A nucleotide sequence encoding the L-lysine decarboxylase which is derived from the *Pseudomonas synxantha* microorganism may have a nucleotide sequence of SEQ ID NO: 10, and also may have a nucleotide sequence having about 75% or more, about 80% or more, about 90% or more, or about 95% or more sequence homology with the nucleotide sequence of SEQ ID NO: 10. However, the polynucleotides encoding the proteins having the lysine decarboxylase activity are not limited to thereto, and the polynucleotides may include all polynucleotides without limitation, as long as the polynucleotides are able to encode the novel protein having the lysine decarboxylase activity of the present invention.

As used herein, the term "homology" refers to a degree of matching with a given amino acid sequence or nucleotide sequence, and the homology may be expressed as a percentage. In the present disclosure, a homologous sequence having activity which is identical or similar to the given amino acid sequence or nucleotide sequence is expressed as "% homology". For example, the homology may be determined by using standard software calculating parameters such as score, identity, similarity, etc., specifically, BLAST 2.0, or by comparing the sequences in a Southern hybridization experiment under stringent conditions as defined, and defining appropriate hybridization conditions may be determined by a method well known to those skilled in the art. (e.g., see Sambrook et al., 1989, infra.).

More specifically, the lysine decarboxylase may have one or more selected from the group consisting of amino acid sequences of SEQ ID NO: 1, SEQ ID NO: 3, SEQ ID NO: 5, SEQ ID NO: 7, and SEQ ID NO: 9. Further, the polynucleotide encoding the protein having the L-lysine decarboxylase activity may have one or more selected from the group consisting of nucleotide sequences of SEQ ID NO: 2, SEQ ID NO: 4, SEQ ID NO: 6, SEQ ID NO: 8, and SEQ ID NO: 10.

In an embodiment of the present invention, it was confirmed that the lysine decarboxylases derived from the above *Pseudomonas* sp. microorganisms show no great changes in their activities at a high pH, and therefore, they have pH stability.

In still another specific aspect of the present invention, provided is a microorganism which is transformed to express the novel protein having the lysine decarboxylase activity. The transformed microorganism may be any one of prokaryotic and eukaryotic microorganisms, as long as it is transformed to express the protein having the corresponding decarboxylase activity. For example, the transformed microorganism may include *Escherichia* sp., *Erwinia* sp., *Serratia* sp., *Providencia* sp., and *Corynebacterium* sp. microorganisms. The microorganism may be specifically a microorganism belonging to *Escherichia* sp. or *Corynebacterium* sp., and more specifically, *E. coli* or *Corynebacterium glutamicum*, but is not limited thereto.

Further, a parent strain of the transformed microorganism may be a microorganism having an improved ability to produce lysine, compared to a wild-type, but is not limited thereto. As used herein, the term "microorganism having improved an ability to produce lysine, compared to a wild-type" refers to a microorganism having increased ability to produce lysine, compared to a natural microorganism or a parent strain, and the microorganism having improved ability to produce lysine is not particularly limited, as long as it is a microorganism having improved ability to produce lysine, compared to a parent strain.

To impart the improved ability to produce lysine compared to the wild-type, a general method of growing microorganisms, such as a method of obtaining auxotrophic mutant strains, analogue-resistant strains, or metabolic control mutant strains having an ability to produce lysine, and a method of producing recombinant strains having enhanced lysine biosynthetic enzyme activities, may be used. In growing of lysine-producing microorganisms, characteristics such as auxotrophy, analogue resistance and metabolic control mutations may be imparted alone or in combination. The enhanced lysine biosynthetic enzyme activity may be imparted alone or in combination. Further, while imparting the characteristics such as auxotrophy, analogue resistance, and metabolic control mutations, the lysine biosynthesis enzyme activity may be also enhanced at the same time. Specifically, a gene encoding the lysine biosynthetic enzyme may include dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh), phosphoenolpyruvate carboxylase gene (ppc), aspartate aminotransferase gene (aspC), and aspartate semialdehyde dehydrogenase gene (asd), but is not limited thereto. A method of imparting or increasing the ability to produce lysine by enhancing the lysine biosynthetic enzyme activity may be performed by inducing mutations in the genes encoding the corresponding enzymes or amplifying the genes to increase intracellular enzyme activities. These methods may be performed by genetic recombination, but are not limited thereto.

The microorganism may be any one of prokaryotic and eukaryotic microorganisms, as long as it has an improved ability to produce lysine, compared to the wild-type. Specifically, the microorganism may be an *Escherichia* sp. microorganism or a *Coryneform* microorganism. The *Escherichia* microorganism may be *Escherichia coli*, *Escherichia albertii*, *Escherichia blattae*, *Escherichia fergusonii*, *Escherichia hermannii*, or *Escherichia vulneris*, but is not limited thereto. More specifically, the *Escherichia* sp. microorganism may be *Escherichia coli*. The *Coryneform* microorganism may include a *Corynebacterium* or *Brevibacterium* sp. microorganism. Further, the *Coryneform* microorganism may be specifically *Corynebacterium glutamicum*, *Corynebacterium thermoaminogenes*, *Brevibacterium flavum*, or *Brevibacterium lactofermentum*, but is not limited thereto.

To transform the microorganism such that the microorganism expresses the protein having the lysine decarboxylase activity, the lysine decarboxylase gene of the present invention may be included as the lysine decarboxylase protein or as a gene expression unit in the microorganism to be transformed. The gene expression unit of the lysine decarboxylase may be operably linked to a vector, and then transformed into the microorganism, or integrated into the chromosome of the microorganism. Specifically, the lysine decarboxylase gene may be operably linked such that the gene is overexpressed by a promoter upstream of the initiation codon.

As used herein, the term "expression unit" refers to a fragment including a promoter operably linked to a polynucleotide encoding a protein, and may further include 3'-UTL, 5'-UTL, poly A tail, etc. As used herein, the term "expression unit" may be interchangeable with "expression cassette".

As used herein, the term "operably linked" refers to a functional linkage between the nucleotide sequence of the gene and a nucleotide sequence having a promoter activity, whereby transcription of the gene encoding lysine decarboxylase is initiated and mediated, indicating that the nucleotide sequence having the promoter activity is operably linked to the lysine decarboxylase gene to control transcriptional activity of the lysine decarboxylase gene.

As used herein, the term "transformation" means an overall action of introducing the lysine decarboxylase gene derived from the *Pseudomonas* sp. microorganism into a host cell, specifically, an *Escherichia* sp. microorganism or a *Coryneform* microorganism, for the expression of the gene in the host cell. In this regard, the lysine decarboxylase gene is a polynucleotide, including DNA and RNA, capable of encoding the lysine decarboxylase. As long as the gene may be introduced into the host cell and expressed therein, it may be introduced in any type. For example, the gene may be introduced into the host cell in an expression cassette which is a polynucleotide structure including by itself whole elements for expressing the gene. The expression cassette includes a promoter which is operably linked to the gene, a transcription termination signal, a ribosome binding site, and a translation termination signal. The expression cassette may be a self-replicable expression vector. The gene also may be introduced into the host cell by itself or in a polynucleotide structure to be operably linked to the sequence necessary for expression in the host cell. The recombinant vector is a means by which DNA is introduced into the host cell to express the protein, and a known expression vector such as a plasmid vector, a cosmid vector, a bacteriophage vector, etc. may be used. The vector may be easily prepared by those skilled in the art according to any known method of using a DNA recombination technique, but is not limited thereto.

The transformation method may be any method of introducing the polynucleotide into cells, and may be performed by selecting an appropriate standard technique known in the art. For example, the method may include electroporation, calcium phosphate co-precipitation, retroviral infection, microinjection, a DEAE-dextran method, a cationic liposome method, etc., but is not limited thereto.

In a specific embodiment, the microorganism having the improved ability to produce lysine is transformed such that the protein having the lysine decarboxylase activity of the present invention is expressed, thereby having excellent ability to produce cadaverine.

In still another specific embodiment of the present invention, provided is use of the novel lysine decarboxylase or the microorganism transformed to express the novel protein having the lysine decarboxylase activity in the production of cadaverine.

The novel lysine decarboxylase and the microorganism transformed to express the novel protein having the lysine decarboxylase activity are the same as described above. In a specific embodiment, it was confirmed that the lysine decarboxylase of the present invention has higher stability against a temperature or pH change than *E. coli*-derived lysine decarboxylase which has commonly been used in the production of cadaverine. Particularly, the novel lysine decarboxylase of the present invention has higher pH stability than *E. coli*-derived lysine decarboxylase, and therefore, it is advantageous in a conversion reaction of lysine into cadaverine. Accordingly, the novel lysine decarboxylase of the present invention and the microorganism transformed to express the novel protein having the lysine decarboxylase activity may be utilized in the production of cadaverine.

In still another aspect of the present invention, provided is a method of preparing cadaverine.

In a specific embodiment of the method of preparing cadaverine of the present invention, the method is a method of preparing cadaverine, including the steps of converting lysine into cadaverine by using the novel protein having the lysine decarboxylase activity or the microorganism transformed to express the protein having the activity; and recovering the converted cadaverine.

The novel protein having the lysine decarboxylase activity and the transformed microorganism are the same as described above. The transformed microorganism may be specifically an *Escherichia* sp. microorganism.

In the step of converting lysine into cadaverine, the novel protein having the lysine decarboxylase activity is extracted from the microorganism expressing the protein, and the enzyme is purified and used to decarboxylate lysine, thereby producing cadaverine. Alternatively, lysine is added to a culture obtained by culturing the transformed microorganism, and the microorganism is used as it is to decarboxylate lysine, thereby converting lysine into cadaverine.

In another specific embodiment of the method of preparing cadaverine of the present invention, provided is a method of preparing cadaverine, including the steps of culturing in a medium the microorganism having an ability to produce cadaverine, wherein the microorganism having improved ability to produce lysine compared to the wild-type is transformed to express the novel protein having the lysine decarboxylase activity; and recovering cadaverine from the microorganism or the culture.

The novel protein having the L-lysine decarboxylase activity and the microorganism having the enhanced ability to produce lysine, compared to the wild-type, are the same as described above.

The culturing may be performed in a suitable medium under culture conditions that are well known in the art. The medium and culture conditions may be easily modified by any person skilled in the art depending on the type of microorganism selected. The culturing method may include batch culture, continuous culture, fed-batch culture, or a combination thereof, but is not limited thereto.

The medium may include a variety of carbon sources, nitrogen sources, and trace elements.

Specifically, for example, the carbon sources may include carbohydrates such as glucose, sucrose, lactose, fructose, maltose, starch, and cellulose; oils such as soybean oil, sunflower oil, castor oil, and coconut oil; fatty acids such as palmitic acid, stearic acid, and linoleic acid; alcohols such as glycerol and ethanol; organic acids such as acetic acid, or combinations thereof. Specifically, glucose may be used as the carbon source, but is not limited thereto. The nitrogen sources may include organic nitrogen sources such as peptone, yeast extract, meat broth, malt extract, corn steep liquor (CSL), and soybean meal, inorganic nitrogen sources such as urea, ammonium sulfate, ammonium chloride, ammonium phosphate, ammonium carbonate, and ammonium nitrate, or combinations thereof, but are not limited thereto. The medium may include, as phosphorus sources, for example, dipotassium hydrogen phosphate, potassium dihydrogen phosphate, and corresponding sodium-containing salts, and metal salts such as magnesium sulfate and iron sulfate, but is not limited thereto. In addition, amino acids, vitamins, and suitable precursors may be included in the medium. The medium or the individual components may be added to the medium in a batch mode or continuous mode. These examples are for illustrative purposes only, and the invention is not intended to be limited thereby.

Further, pH of the medium may be adjusted during the culture by adding a compound such as ammonium hydroxide, potassium hydroxide, ammonia, phosphoric acid, or sulfuric acid by a suitable method. The generation of air bubbles may be inhibited during the culture by using an antifoaming agent such as fatty acid polyglycol ester. To maintain an aerobic condition in the medium, oxygen or oxygen-containing gas (e.g., air) may be injected into the culture. The temperature of the culture may be generally 20° C. to 45° C., for example, 25° C. to 40° C. The culturing may be continued until the production of lysine decarboxylase reaches a desired level, for example, for 10 hours to 160 hours.

A method of recovering cadaverine may be performed by, for example, collecting or recovering the produced cadaverine from the medium by an appropriate method known in the art according to a batch mode, a continuous mode, or a fed-batch mode. In this recovery method, centrifugation, filtration, ion exchange chromatography, crystallization, etc. may be used. For example, biomass may be removed from the culture by low-speed centrifugation, and a resulting supernatant may be purified by ion exchange chromatography.

Further, the method of preparing cadaverine may further include the step of recovering the lysine decarboxylase from the microorganism or the medium.

A method of recovering the lysine decarboxylase from the microorganism or the medium may be performed by, for example, collecting or recovering the produced lysine decarboxylase from the microorganism or the medium by an appropriate method known in the art according to a batch mode, a continuous mode, or a fed-batch mode. In this recovery method, centrifugation, filtration, ion exchange chromatography, crystallization, etc. may be used. For example, biomass may be removed from the culture by low-speed centrifugation, and a resulting supernatant may be purified by ion exchange chromatography. Further, lysine decarboxylase may be recovered from a cell lysate which is obtained by disrupting the microorganism in the medium. The cell lysate may be obtained by using an appropriate method known in the art. For example, a physical homogenizer or a commercially available cell lysis buffer may be used. The lysine decarboxylase may be obtained from the cell lysate by an appropriate method known in the art, such as centrifugation, etc.

Advantageous Effects of the Invention

A novel protein having lysine decarboxylase activity derived from a *Pseudomonas* sp. Microorganism, provided in the present invention, may have stable activity even under pH changes, and therefore, the protein may be efficiently used in a conversion reaction of lysine into cadaverine, thereby being widely used in the production of cadaverine.

DESCRIPTION OF THE DRAWINGS

FIG. 2 is an image of SDS-PAGE gel showing expression results of PtLDC, and PtLDC with an N-terminal his-tag;

MODE OF THE INVENTION

Figure 1:
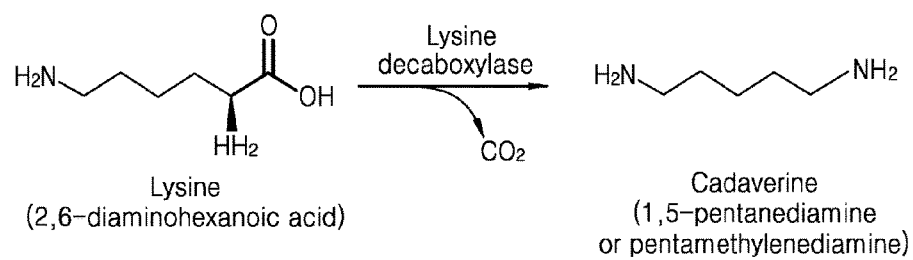
FIG. 1 shows a reaction mechanism of lysine decarboxylase which produces cadaverine from lysine.

Hereinafter, the present invention will be described in more detail with reference to Examples. However, these Examples are for illustrative purposes only, and the scope of the present invention is not intended to be limited by these Examples.

Example 1

Selection of Novel Lysine Decarboxylase for Producing Cadaverine 1-1. Selection of Lysine Decarboxylase Derived from *Pseudomonas Thermotolerans*

To select a novel lysine decarboxylase to be used in the production of cadaverine, a BLAST program (http://blast.ncbi.nlm.nih.gov/Blast.cgi?PROGRAM=blastn&PAGE_TYPE=BlastSearch&LINK_LOC=blasthome) provided by the National Center for Biotechnology Information (NCBI), USA was used to search for lysine decarboxylase derived from a thermophilic bacterium which has high similarity to a peptide sequence of an active site of lysine decarboxylase derived from *E. coli*. In detail, a BLAST search was carried out, based on a total of 31 peptide sequences (GRVEGKVIYETQSTHKLLAAF-SQASMIHVKG: SEQ ID NO: 12) each including 15 amino acids at the N-terminus and the C-terminus centered around the 367$^{th}$ lysine which is the main amino acid of lysine decarboxylase derived from *E. coli*. As a result, it was confirmed that *Escherichia, Shigella, Enterobacteria, Edwardsiella, Klebsiella, Serratia, Yersinia, Yokenella, Raoultella, Ceratitis, Salmonella, Sutterella, Shimwellia, Vibrio*, and *Pseudomonas* sp. microorganisms have high homology. The search was aimed at finding lysine decarboxylase having high thermal stability while having activity similar to that of lysine decarboxylase of *E. coli*. In general, proteins found in thermophilic bacteria are known to have high thermal stability, and therefore, of the microorganisms found from the search, *Pseudomonas thermotolerans* known as a thermophilic (46~60° C.) microorganism was selected.

1-2. Selection of Lysine Decarboxylase Derived from Various *Pseudomonas* sp. Microorganisms To select lysine decarboxylases derived from *Pseudomonas* sp. microorganisms other than *Pseudomonas thermotolerans*, four microorganisms (*Pseudomonas alcaligenes, Pseudomonas resinovorans, Pseudomonas putida*, and *Pseudomonas synxantha*) showing low homology between *Pseudomonas* sp. were selected. Nucleotide and genome programs provided by the National Center for Biotechnology Information (NCBI), USA (http://www.ncbi.nlm.nih.gov/) were used to identify nucleotide and amino acid sequences of lysine decarboxylases derived from the four *Pseudomonas* sp. microorganisms selected as above.

The following Table 1 shows amino acid sequence homology of lysine decarboxylase derived from *Pseudomonas* sp.

|       | PtLDC | PaLDC | PrLDC | PpLDC | PxLDC |
|-------|-------|-------|-------|-------|-------|
| PtLDC |       | 87%   | 86%   | 81%   | 84%   |
| PaLDC | 87%   |       | 89%   | 80%   | 85%   |
| PrLDC | 86%   | 89%   |       | 77%   | 83%   |
| PpLDC | 81%   | 80%   | 77%   |       | 84%   |
| PxLDC | 84%   | 85%   | 83%   | 84%   |       |

PtLDC: lysine decarboxylase derived from *Pseudomonas thermotolerans* (*P. thermotolerans*)
PaLDC: lysine decarboxylase derived from *Pseudomonas alcaligenes* (*P. alcaligenes*)
PrLDC: lysine decarboxylase derived from *Pseudomonas resinovorans* (*P. resinovorans*)
PpLDC: lysine decarboxylase derived from *Pseudomonas putida* (*P. putida*)
PxLDC: lysine decarboxylase derived from *Pseudomonas synxantha* (*P. synxantha*)

Example 2

Preparation of *E. coli* Introduced with Lysine Decarboxylase Gene Derived from *Pseudomonas Thermotolerans* and Analysis of Activity of Lysine Decarboxylase Expressed Therefrom 2-1. Transformation of *E. coli* with Lysine Decarboxylase Gene Derived from *Pseudomonas thermotolerans*

To introduce the lysine decarboxylase gene derived from *Pseudomonas thermotolerans* into *E. coli* and express the gene therefrom, cloning of a recombinant gene was performed. Genetic information on *Pseudomonas thermotolerans* was obtained from genomic data of the NCBI (http://www.ncbi.nlm.nih.gov/genome/).

The genomic DNA of *Pseudomonas thermotolerans* was obtained, and then used as a template to amplify a *Pseudomonas thermotolerans*-derived lysine decarboxylase gene (ptldc) by polymerase chain reaction (PCR). To perform PCR, primers of 5_LDC_NdeI (AATATACATATGTA-CAAAGACCTCCAATTCCCC) (SEQ ID NO: 13) and 3_LDC_XhoI (AATATACTCGAGTCAGATCTTGAT-GCAGTCCACCG) (SEQ ID NO: 14) and PfuUltra™ DNA polymerase (Stratagene, USA) were used to perform PCR for 30 cycles under conditions of 94° C.: 30 sec, 55° C.: 30 sec, and 72° C.: 2 min. As a result, amplified ptldc (SEQ ID NO: 2) was obtained. Further, to express *Pseudomonas thermotolerans*-derived lysine decarboxylase with an N-terminal His-tag, primers of 5_LDC_BamHI (AATATAG-GATCCGTACAAAGACCTCCAATTCCCC) (SEQ ID NO: 15) and 3_LDC_SacI (AATATAGAGCTCTCAGATCTT-GATGCAGTCCACCG) (SEQ ID NO: 16) were used to perform PCR in the same manner as the above PCR method. Next, each ptldc gene obtained from PCR was inserted into an *E. coli* expression vector, pET-Deut1. Thereafter, each plasmid cloned with the ptldc gene was inserted into *E. coli* Rosetta by a heat shock transformation method. Each of the transformed *E. coli* was cultured in a 50 ml liquid LB medium (containing 50 mg/ml ampicillin) at 37° C. When an OD600 value reached 0.8, 0.4 mM isopropyl β-D-1-thiogalactopyranoside (IPTG) was added thereto and incubated at 18° C. for 48 hours to induce expression. Each *Pseudomonas thermotolerans*-derived lysine decarboxylase (PtLDC) thus completely expressed was identified by SDS-PAGE (FIG. 2). The results of SDS-PAGE showed that PtLDC and PtLDC with His-tag expressed at a low temperature were overexpressed as soluble proteins (Lanes 2 and 4 of FIG. 2).

The *E. coli* Rosetta transformed with the plasmid including the ptldc (SEQ ID NO: 2) was designated as '*Escherichia coli* CC04-0055', and deposited at the Korean Culture Center of Microorganisms (KCCM) on Jul. 24, 2014 under the Accession number KCCM11559P.

2-2. Analysis of Activity of *Pseudomonas thermotolerans*-Derived Lysine Decarboxylase Expressed in *E. coli*

(1) Analysis of Reactivity of Lysine Decarboxylase

Figure 3:
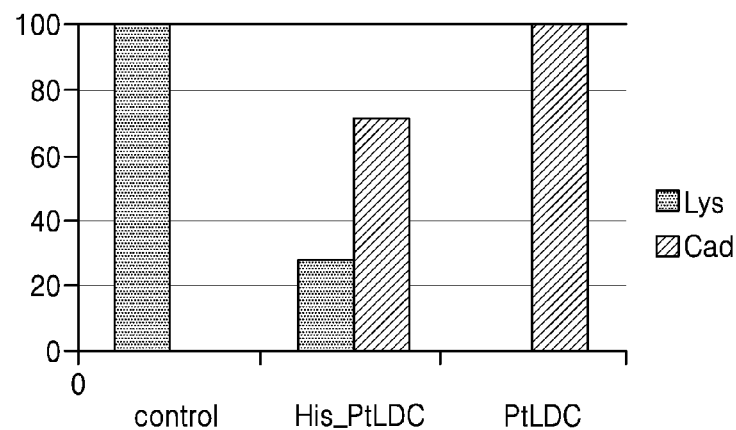
FIG. 3 shows PtLDC reactivity of converting lysine into cadaverine.

To investigate reactivities of PtLDC and PtLDC with the His-tag, 50 ml of soluble protein, 100 mM pyridoxalphosphate (pyridoxal-phosphate, PLP), and 250 mM lysine were reacted in a volume of 200 ml at 46° C. for 2 hours. A reaction buffer solution was 50 mM sodium phosphate at pH 6.2. A microorganism into which an empty vector was introduced was used as a control, and amounts of lysine and cadaverine were analyzed (FIG. 3). High-performance liquid chromatography (Waters, Milford, Mass.) was performed to analyze accurate amounts of lysine and cadaverine in a 2414 Refractive Indes Detector (Waters, Milford, Mass.). Lysine-HCl reagent and 1,5-diaminopentane (cadaverine) reagent were purchased from Sigma (St. Louis, Mo.), and a mobile phase consisting of 1 mM citric acid, 10 mM tartaric acid, 24 mM ethylenediamine, and 5% acetonitrile was used to separate and quantify the two materials in an IonoSpher C3-100 mm, 5 mm column. The control showed no production of cadaverine. PtLDC with the N-terminal His-tag showed 72% lysine conversion, and PtLDC showed 100% lysine conversion, indicating production of cadaverine.

Figure 4:
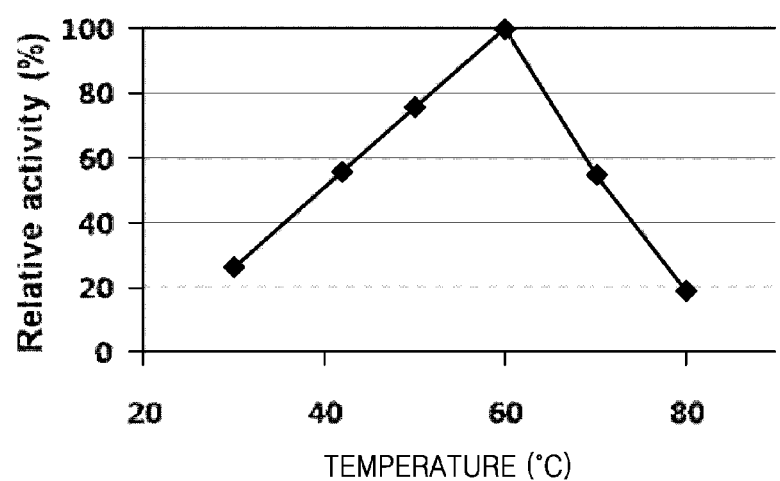
FIG. 4 shows a relative enzymatic activity of PtLDC according to varying temperature.

(2) Analysis of Activity of Lysine Decarboxylase According to Temperature and pH To analyze enzymatic characteristics of PtLDC under various temperature conditions (30° C., 42° C., 50° C., 60° C., 70° C., and 80° C.), relative activities were compared. When PtLDC was diluted and reacted with 250 mM lysine substrate at 60° C. for 30 minutes, 42 mM cadaverine was found to be produced. In this regard, concentrations of cadaverine were analyzed by using 50 mM sodium phosphate buffer (pH 6.2) as a buffer solution, and an equal amount of the enzyme under the same reaction conditions, except that temperature conditions were 30° C., 42° C., 50° C., 70° C., and 80° C., and compared with the amount of cadaverine produced at a reaction temperature of 60° C. (FIG. 4). As shown in FIG. 4, PtLDC showed the highest activity at 60° C. Further, PtLDC maintained 80% or more of the activity at a temperature of 55° C.~65° C.

Figure 5:
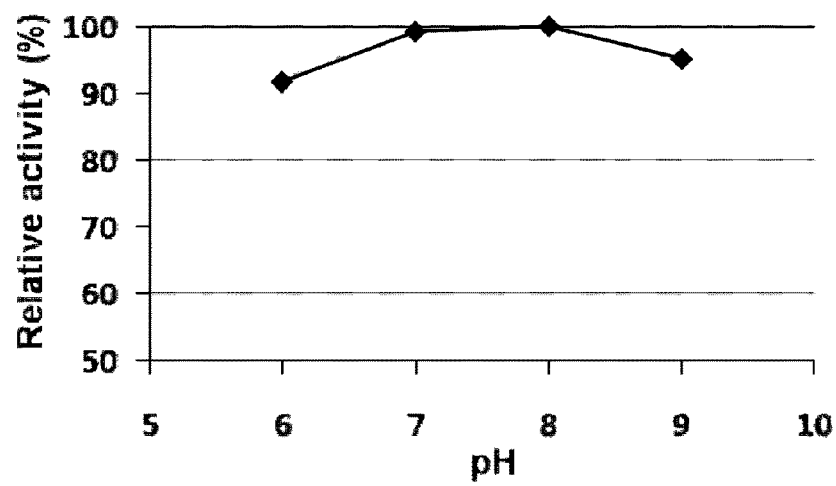
FIG. 5 shows a relative enzymatic activity of PtLDC according to varying pH.

Additionally, activity of lysine decarboxylase was evaluated under various pH conditions (6.2, 7.0, 8.0, and 9.0). The temperature condition was fixed at 60° C., and an equal amount of the enzyme was used under the same reaction conditions, except that 50 mM sodium phosphate buffer (pH 6.2), 50 mM tris buffer (pH 7.0), 100 mM potassium phosphate buffer (pH 8.0), and 50 mM tris buffer (pH 9.0) were used. Reactivities of lysine decarboxylase at different pHs were compared (FIG. 5). PtLDC showed the highest activity at pH 8.0, and maintained 90% or more of the activity at pH 6 to pH 9. An amount of cadaverine produced at each pH condition was compared with that of cadaverine produced at pH 8 (FIG. 5). The experimental result showed that PtLDC has high stability against pH change or high pH.

Example 3

Preparation of *E. coli* Introduced with Lysine Decarboxylase Gene Derived from *Pseudomonas Alcaligenes* and Analysis of Activity of Lysine Decarboxylase Expressed Therefrom 3-1. Transformation of *E. coli* with Lysine Decarboxylase Gene Derived from *Pseudomonas alcaligenes*

To clone a lysine decarboxylase gene (paldc) derived from *Pseudomonas alcaligenes*, primers of 5_PaLDC_NdeI (AATATACATATGTACAAAGACCTGAA GTTCCCCATCC) (SEQ ID NO: 17) and 3_PaLDC_XhoI (AATATACTCGAGTCACTCCCTTATGCAATCAACGG-TATAGC) (SEQ ID NO: 18) and purified genomic DNA of *Pseudomonas alcaligenes* as a template were used to perform PCR. Pfu DNA polymerase was used as a polymerase, and PCR was performed for 30 cycles under conditions of 94° C.: 30 sec, 55° C.: 30 sec, and 72° C.: 2 min. As a result, an amplified paldc gene (SEQ ID NO: 4) was obtained.

Figure 6:
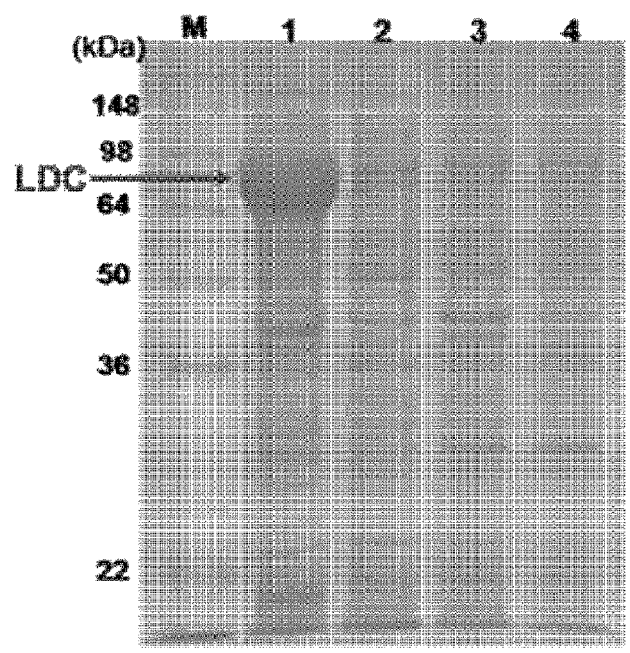
FIG. 6 is an image of SDS-PAGE gel showing PaLDC and PrLDC expression.

The obtained paldc gene was expressed at a low temperature in *E. coli* in the same manner as in Example 2-1, and identified by SDS-PAGE (FIG. 6). As shown in FIG. 6, *Pseudomonas alcaligenes*-derived lysine decarboxylase (PaLDC) was mostly expressed as insoluble protein, and no soluble protein was observed on the SDS-PAGE gel (FIG. 6, see Lanes 1 and 2).

3-2. Analysis of Activity of *Pseudomonas alcaligenes*-Derived Lysine Decarboxylase Expressed in *E. coli*

(1) Analysis of Reactivity of Lysine Decarboxylase

Figure 7:
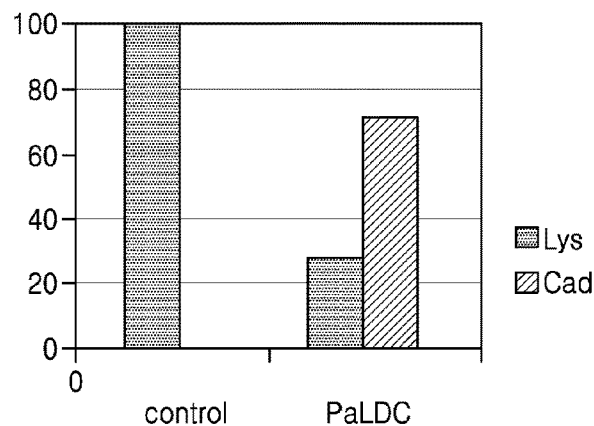
FIG. 7 shows PaLDC reactivity of converting lysine into cadaverine.

To investigate reactivity of PaLDC, a cell lysate of PaLDC obtained in Example 3-1 was centrifuged at 13,000 rpm for 15 minutes to obtain a supernatant (soluble protein), which was used in conversion of lysine. 50 μl of the soluble protein, 100 mM PLP, and 250 mM lysine were reacted in 50 mM sodium phosphate buffer (pH 6.2) in a reaction volume of 200 μl at 46° C. for 2 hours. As a result, 70% lysine was found to be converted into cadaverine by PaLDC (FIG. 7).

Figure 8:
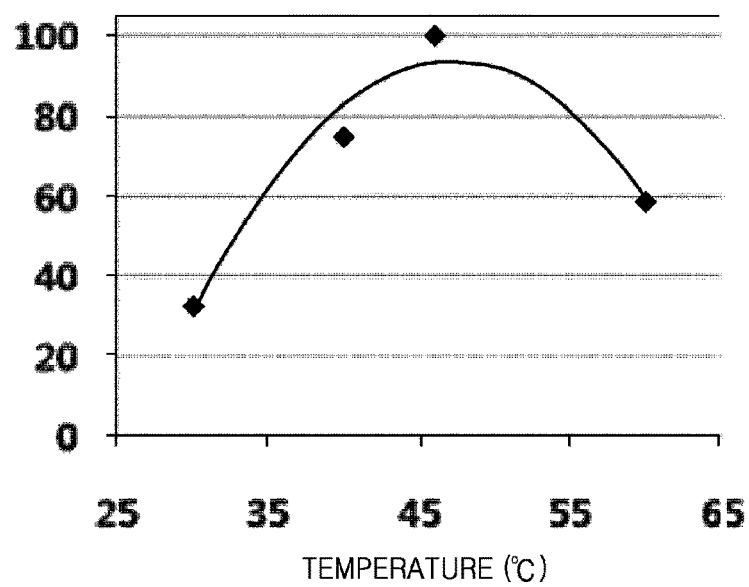
FIG. 8 shows a relative enzymatic activity of PaLDC according to varying temperature.

(2) Analysis of Activity of Lysine Decarboxylase According to Temperature and pH To find an optimum temperature condition for activity of *Pseudomonas alcaligenes*-derived lysine decarboxylase, enzymatic activities were evaluated under temperature conditions of 30° C., 40° C., 46° C., and 60° C. in the same manner as in Example 2-2. As a result, PaLDC was found to have the highest activity at 50° C. (FIG. 8).

Figure 9:
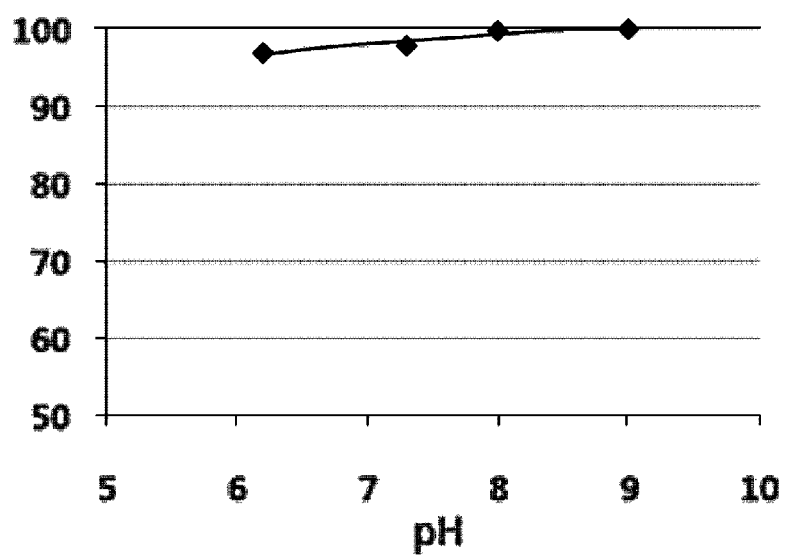
FIG. 9 shows a relative enzymatic activity of PaLDC according to varying pH.

The activity of *Pseudomonas alcaligenes*-derived lysine decarboxylase under different pH conditions was evaluated in the same manner as in Example 2-2. As a result, PaLDC had the highest stability at pH 8 and pH 9, and maintained 95% or more of the activity at pH 6 (FIG. 9).

Example 4

Preparation of E. coli Introduced with Lysine Decarboxylase Gene Derived from Pseudomonas Resinovorans and Analysis of Activity of Lysine Decarboxylase Expressed Therefrom

4-1. Transformation of E. coli with Lysine Decarboxylase Gene Derived from Pseudomonas resinovorans To clone a lysine decarboxylase gene (prldc) derived from Pseudomonas resinovorans, primers of 5_PrLDC_Ndel (AATATACATATGTACAAAGAGCTC AAGTTC-CCCGTCCTC) (SEQ ID NO: 19) and 3_PrLDC_Xhol (AATATACTCGAG TTATTCCCTGATGCAGTCCACT-GTA TAGC) (SEQ ID NO: 20) and purified genomic DNA of Pseudomonas resinovorans as a template were used to perform PCR. PCR was performed by using the same polymerase under the same PCR conditions as in Example 3-1. As a result, amplified prldc (SEQ ID NO: 6) was obtained.

The obtained prldc gene was expressed at a low temperature in E. coli in the same manner as in Example 2-1, and identified by SDS-PAGE (FIG. 6; Lanes 3 and 4). As a result, PrLDC was found to be hardly expressed at a low temperature.

Figure 10:
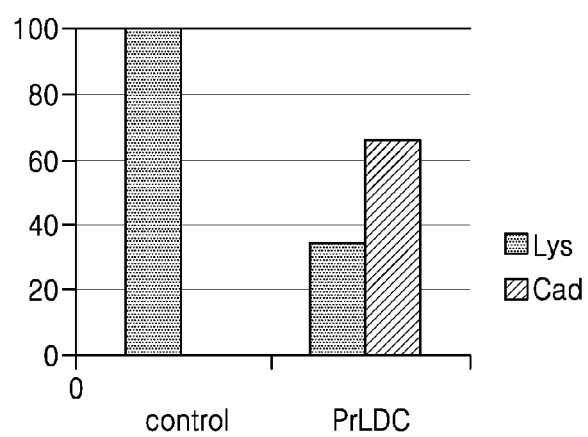
FIG. 10 shows PrLDC reactivity of converting lysine into cadaverine.

4-2. Analysis of Activity of Pseudomonas resinovorans-Derived Lysine Decarboxylase Expressed in E. coli (1) Analysis of Reactivity of Lysine Decarboxylase To investigate reactivity of lysine decarboxylase (PrLDC) derived from Pseudomonas resinovorans, a cell lysate of PrLDC obtained in Example 4-1 was centrifuged at 13,000 rpm for 15 minutes to obtain a supernatant, which was used in conversion of lysine. 50 μl of the soluble protein, 100 mM PLP, and 250 mM lysine were reacted in 50 mM sodium phosphate buffer (pH 6.2) in a reaction volume of 200 μl at 46° C. for 2 hours. As a result, 66% cadaverine was produced (FIG. 10).

Figure 11:
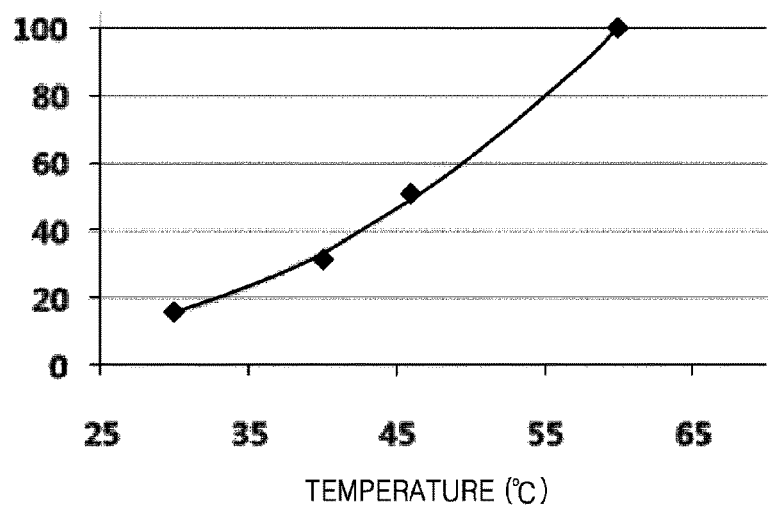
FIG. 11 shows a relative enzymatic activity of PrLDC according to varying temperature.

(2) Analysis of Activity of Lysine Decarboxylase According to Temperature and pH To find an optimum temperature condition for activity of PrLDC, enzymatic activities were evaluated under temperature conditions of 30° C., 40° C., 46° C., and 60° C. in the same manner as in Example 2-2. As a result, PrLDC was found to have the highest activity at 60° C. (FIG. 11).

Figure 12:
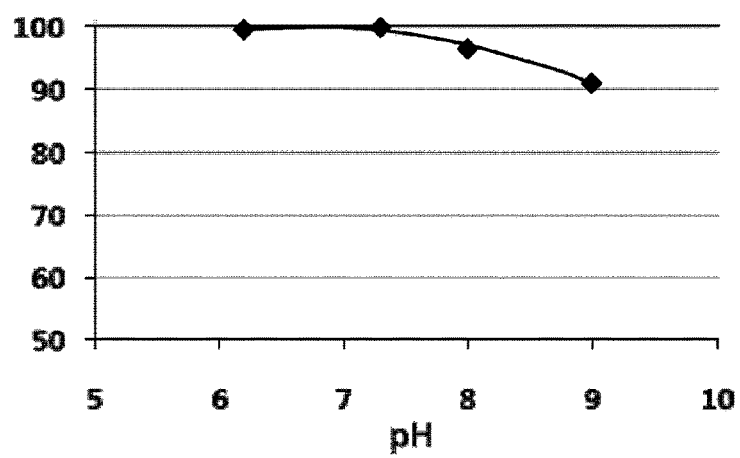
FIG. 12 shows a relative enzymatic activity of PrLDC according to varying pH.

The activity of PrLDC under different pH conditions was evaluated in the same manner as in Example 2-2. As a result, PrLDC had the highest stability at pH 6, and maintained 90% or more of the activity at pH 9 (FIG. 12).

Example 5

Preparation of E. coli Introduced with Lysine Decarboxylase Gene Derived from Pseudomonas putida and Analysis of Activity of Lysine Decarboxylase Expressed Therefrom

5-1. Transformation of E. coli with Lysine Decarboxylase Gene Derived from Pseudomonas putida To clone a lysine decarboxylase gene (ppldc) derived from Pseudomonas putida, primers of 5_PpLDC_Ndel (AATATACATATGTACAAAGACCTCCAA TTCCCC) (SEQ ID NO: 21) and 3_PpLDC_Xhol (AATATACTC-GAGTCACTCCCTTATGCAATCAACGGTATAGC) (SEQ ID NO: 22) and purified genomic DNA of Pseudomonas putida as a template were used to perform PCR. Pfu DNA polymerase was used as a polymerase, and PCR was performed for 30 cycles under conditions of 94° C.: 30 sec, 55° C.: 30 sec, and 72° C.: 2 min. As a result, an amplified ppldc gene (SEQ ID NO: 8) was obtained.

Figure 13:
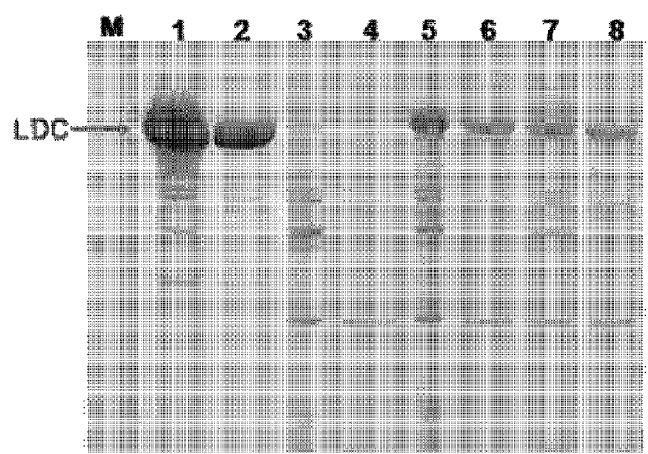
FIG. 13 is an image of SDS-PAGE gel showing expression results of EcLDC, PpLDC, PtLDC, and PxLDC.

The obtained ppldc gene was expressed at a low temperature in E. coli in the same manner as in Example 2-1, and identified by SDS-PAGE (FIG. 13). As shown in Lanes 3 and 4 of FIG. 13, Pseudomonas putida-derived lysine decarboxylase (PpLDC) was found to be hardly expressed at a low temperature.

A cell lysate was centrifuged at 13,000 rpm for 15 minutes, and a supernatant was used in a conversion reaction of lysine.

Figure 14:
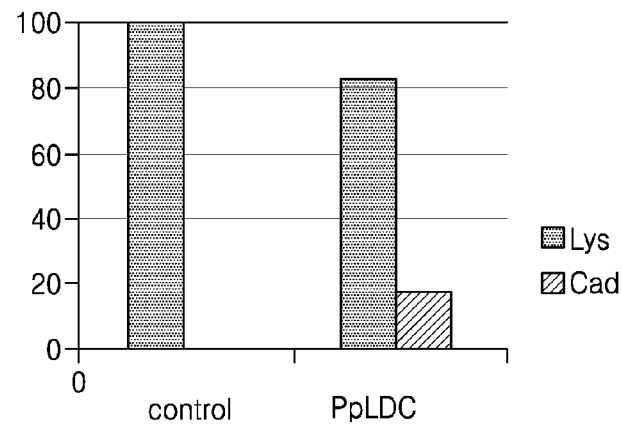
FIG. 14 shows PpLDC reactivity of converting lysine into cadaverine.

5-2. Analysis of Activity of Pseudomonas putida-Derived Lysine Decarboxylase Expressed in E. coli (1) Analysis of Reactivity of Lysine Decarboxylase To investigate reactivity of PpLDC, the cell lysate of PpLDC obtained in Example 5-1 was centrifuged at 13,000 rpm for 15 minutes to obtain a supernatant, which was used in conversion of lysine. 50 μl of the soluble protein, 100 mM PLP, and 250 mM lysine were reacted in 50 mM sodium phosphate buffer (pH 6.2) in a reaction volume of 200 μl at 46° C. for 2 hours. As a result, 16% cadaverine was produced (FIG. 14).

Figure 15:
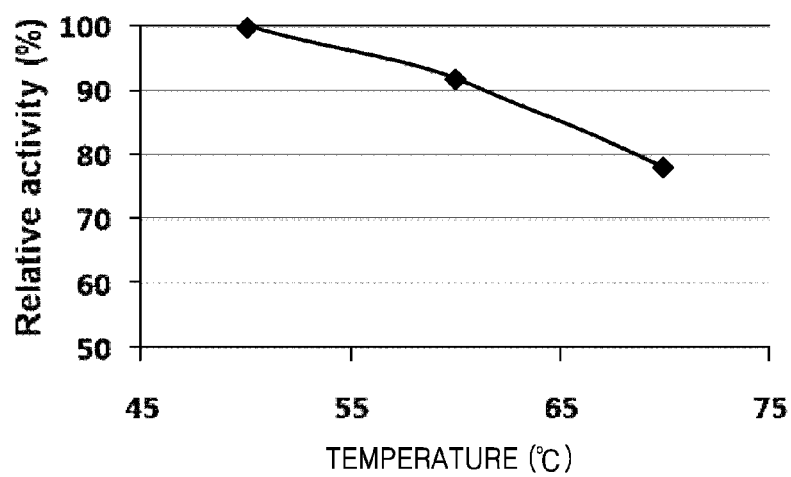
FIG. 15 shows a relative enzymatic activity of PpLDC according to varying temperature.

(2) Analysis of Activity of Lysine Decarboxylase According to Temperature and pH To find an optimum temperature condition for activity of PpLDC, enzymatic activities were evaluated under temperature conditions of 50° C., 60° C., and 70° C. in the same manner as in Example 2-2. As a result, PpLDC was found to have the highest activity at 50° C. (FIG. 15).

Figure 16:
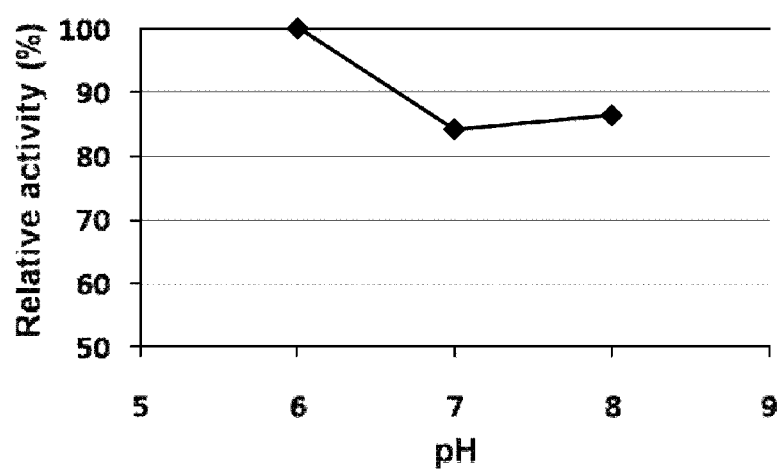
FIG. 16 shows a relative enzymatic activity of PpLDC according to varying pH.

The activity of PpLDC under different pH conditions was evaluated in the same manner as in Example 2-2. As a result, PpLDC showed the highest activity at pH 6, and its reactivity decreased with increasing pH (FIG. 16).

Example 6

Preparation of E. coli Introduced with Lysine Decarboxylase Gene Derived from Pseudomonas synxantha and Analysis of Activity of Lysine Decarboxylase Expressed Therefrom

6-1. Transformation of E. coli with Lysine Decarboxylase Gene Derived from Pseudomonas synxantha To clone a lysine decarboxylase gene (pxldc) derived from Pseudomonas synxantha, primers of 5_PxLDC_Ndel (AATATACATATGTACAAAGACCTCCAA TTCCCC) (SEQ ID NO: 23) and 3_PxLDC_Xhol (AATATACTC-GAGTCACTCCCTTATGCAATCAACGGTATAGC) (SEQ ID NO: 24) and purified genomic DNA of Pseudomonas synxantha as a template were used to perform PCR. Pfu DNA polymerase was used for gene amplification, and PCR was performed for 30 cycles under conditions of 94° C.: 30 sec, 45° C.: 30 sec, and 72° C.: 2 min to obtain amplified pxldc (SEQ ID NO: 10).

The obtained pxldc gene was expressed at a low temperature in E. coli in the same manner as in Example 2-1, and identified by SDS-PAGE (FIG. 13). As shown in Lanes 7 and 8 of FIG. 13, Pseudomonas synxantha-derived lysine decarboxylase (PxLDC) was found to be overexpressed as soluble protein at a low temperature.

Figure 17:
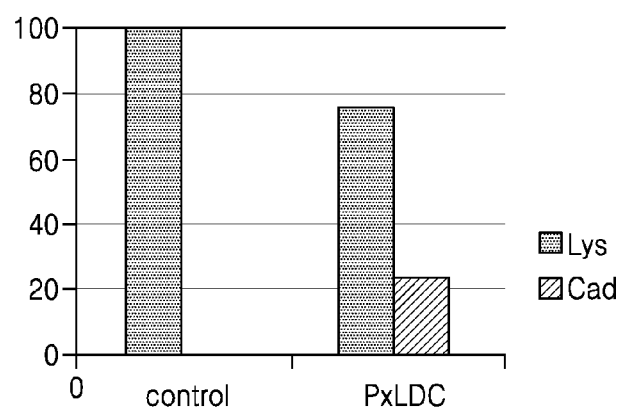
FIG. 17 shows PxLDC reactivity of converting lysine into cadaverine.

6-2. Analysis of Activity of Pseudomonas synxantha-derived Lysine Decarboxylase Expressed in E. coli (1) Analysis of Reactivity of PxLDC To investigate reactivity of PxLDC, the cell lysate of PxLDC obtained in Example 6-1 was centrifuged at 13,000 rpm for 15 minutes to obtain a supernatant, which was used in conversion of lysine. 50 μl of the soluble protein, 100 mM PLP, and 250 mM lysine were reacted in 50 mM sodium phosphate buffer (pH 6.2) in a reaction volume of 200 μl at 46° C. for 2 hours. As a result, 25% cadaverine was produced (FIG. 17).

(2) Analysis of Activity of Lysine Decarboxylase According to pH

Figure 18:
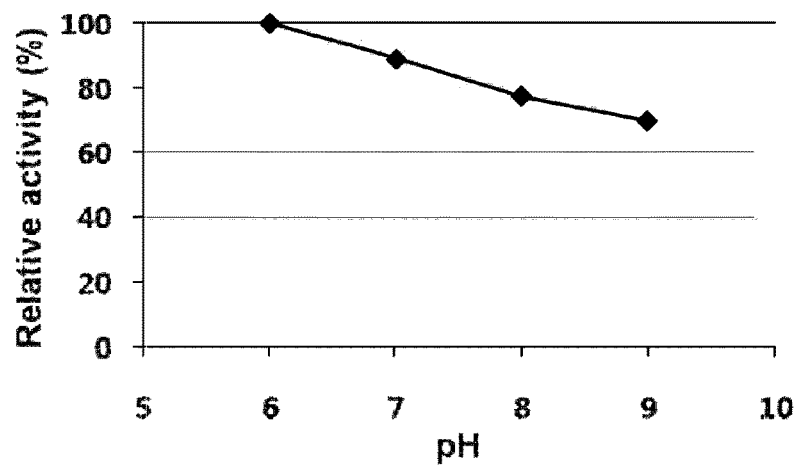
FIG. 18 shows a relative enzymatic activity of PxLDC according to varying pH.

To find an optimum pH condition for PxLDC, enzymatic activities were evaluated under different pH conditions in the same manner as in Example 2-2 (FIG. 18). As a result, PxLDC showed the highest activity at pH 6, and its reactivity decreased with increasing pH.

Example 7

Comparison of Activity between *E. coli*-derived Lysine Decarboxylase and *Pseudomonas thermotolerans*-Derived Lysine Decarboxylase 7-1. Cloning and Expression of *E. coli*-derived Lysine Decarboxylase An *E. coli* lysine decarboxylase gene, cadA, was cloned to express EcLDC (SEQ ID NO: 11). Homology between PtLDC and EcLDC amino acid sequences is 36%. A cadA gene-cloned plasmid was inserted into *E. coli* K-12 BL21, and incubated at 37° C. for 4 hours to induce expression. EcLDC thus completely expressed was identified by SDS-PAGE (FIG. 13; Lanes 1 and 2). As a result, EcLDC was found to be overexpressed as soluble protein.

Figure 19:
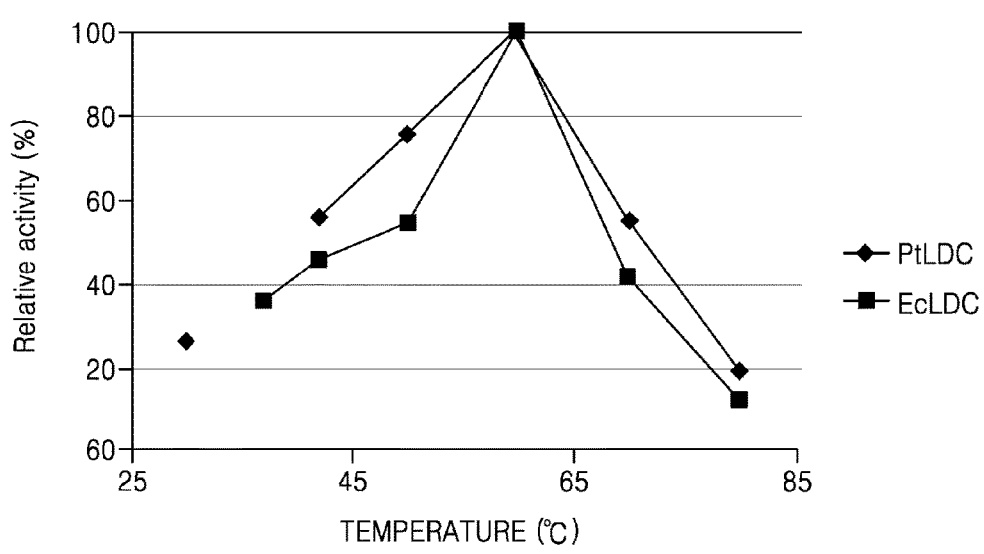
FIG. 19 shows respective relative enzymatic activities of EcLDC and PtLDC according to varying temperature.

7-2. Comparison of Relative Enzymatic Activity Between EcLDC and PtLDC (1) Comparison of Activity According to Temperature Relative enzymatic activity (relative activity) was compared between EcLDC and PtLDC under various temperature conditions (37° C., 42° C., 50° C., 60° C., 70° C., and 80° C.) in the same manner as in Example 2-2 (FIG. 19).

As a result, both EcLDC and PtLDC were found to show the highest activity at 60° C. EcLDC had 54% relative activity at 50° C. (when the activity of EcLDC at 60° C. was taken as 100%), and EcLDC had 12% relative activity at 80° C. PtLDC had 76% relative activity at 50° C. (when the activity of PtLDC at 60° C. was taken as 100%), and PtLDC had 19% relative activity at 80° C. The activity of PtLDC was found to be well maintained at a high temperature. In conclusion, both of the two enzymes showed a great difference in their activities depending on temperature, and the relative activity of PtLDC was well maintained, compared to EcLDC.

(2) Comparison of Activity According to pH

Figure 20:
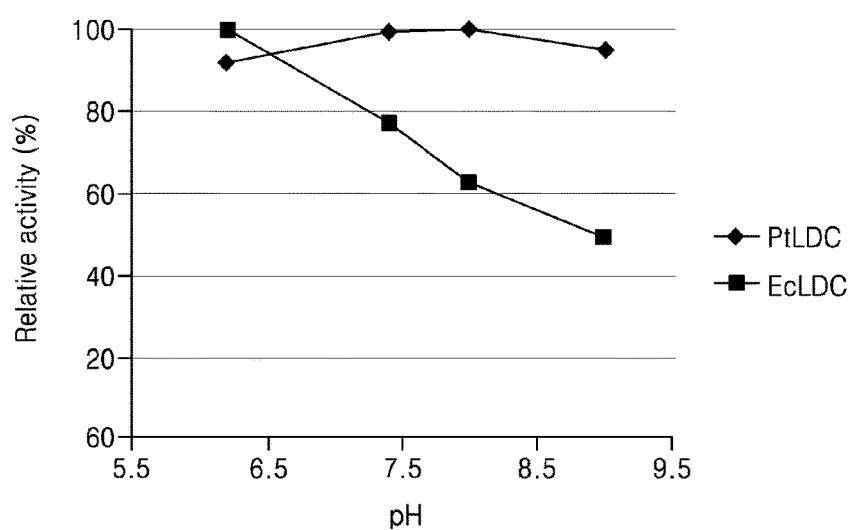
FIG. 20 shows respective relative enzymatic activities of EcLDC and PtLDC according to varying pH.

Additionally, activity was evaluated under various pH conditions (6.2, 7.4, 8.0, and 9.0) in the same manner as in Example 2-2 (FIG. 20). As a result, EcLDC showed the highest activity at pH 6, and enzymatic activity of EcLDC greatly decreased with increasing pH. At pH 9, EcLDC maintained 50% of the activity. In contrast, PtLDC showed no great change in the activity according to pH, and PtLDC maintained 90% or more of the activity at pH 6.2-9. Accordingly, it was evaluated that PtLDC showed higher stability against temperature and pH than EcLDC.

(3) Comparison of Activity Between PtLDC and EcLDC

When PtLDC and EcLDC proteins were quantified to evaluate specific activity (unit/mg), PtLDC showed a value of 10060 (unit/mg), and EcLDC showed a value of 36335 (unit/mg). When their reactivities were compared, EcLDC showed about 3.6 times higher activity than PtLDC. Further, when an optimal temperature was compared between the enzymes, both two enzymes showed optimal reactions at 60° C., and their activities greatly decreased with varying temperature. However, when optimal pH conditions were compared, EcLDC showed higher specific inactivity with increasing pH, and PtLDC showed no great change in the enzymatic activity according to pH change.

EcLDC has higher activity than PtLDC. However, activity of EcLDC may be greatly influenced by pH change, as pH increases by reaction of lysine decarboxylase. PtLDC has higher pH stability than EcLDC, which is advantageous in the lysine conversion reaction. Commercial production of cadaverine by bioconversion of lysine requires pH adjustment by acid treatment, but PtLDC may mitigate the need for pH titration. It is expected that production costs required for the bioconversion of cadaverine may be reduced.

Depositary institution: Korean Culture Center of Microorganisms (KCCM)

Accession number: KCCM11559P

Date of deposit: Jul. 24, 2014

The invention claimed is:

1. A microorganism which is transformed with a polynucleotide encoding a protein having lysine decarboxylase activity, comprising the amino acid sequence of SEQ ID NO: 1 or the amino acid sequence having 90% or more homology therewith to express the protein, wherein the protein having lysine decarboxylase activity is from a *Pseudomonas* sp. and wherein the microorganism is an *Escherichia* sp. microorganism.

2. The microorganism of claim 1, wherein the polynucleotide has the nucleotide sequence of SEQ ID NO: 2.

3. The microorganism of claim 1, wherein the protein having lysine decarboxylase activity maintains 90% or more of the activity at pH 9 compared to that at pH 6.

4. A method of preparing cadaverine, comprising the steps of:
converting lysine into cadaverine by using the microorganism of claim 1; and
recovering the cadaverine.

5. The method of preparing cadaverine of claim 4, wherein the step of converting comprises:
culturing the microorganism in a medium; and
recovering cadaverine from the microorganism or the medium.

6. The method of preparing cadaverine of claim 4, the protein having the lysine decarboxylase activity comprises the amino acid sequence having 95% or more homology with the amino acid sequence of SEQ ID NO: 1.

7. The method of preparing cadaverine of claim 4, wherein the polynucleotide has a nucleotide sequence of SEQ ID NO: 2.

8. The microorganism of claim 1, wherein the protein having the lysine decarboxylase activity comprises the amino acid sequence having 95% or more homology with the amino acid sequence of SEQ ID NO: 1.

* * * * *